(12) United States Patent
Bernardon

(10) Patent No.: US 6,706,725 B1
(45) Date of Patent: Mar. 16, 2004

(54) VITAMIN D ANALOGUES

(75) Inventor: Jean-Michel Bernardon, Nice (FR)

(73) Assignee: Galderma Research & Development, S.N.C., Valbonne (FR)

( * ) Notice: Subject to any disclaimer, the term of this patent is extended or adjusted under 35 U.S.C. 154(b) by 0 days.

(21) Appl. No.: 10/130,794

(22) PCT Filed: Nov. 22, 2000

(86) PCT No.: PCT/FR00/03250

§ 371 (c)(1),
(2), (4) Date: Sep. 5, 2002

(87) PCT Pub. No.: WO01/38320

PCT Pub. Date: May 31, 2001

(30) Foreign Application Priority Data

Nov. 24, 1999 (FR) .............................. 99 14783

(51) Int. Cl.⁷ .................. C07D 213/02; A61K 31/44
(52) U.S. Cl. .................. 514/277; 514/352; 514/357; 514/354; 514/438; 514/445; 546/309; 546/314; 546/334; 546/339; 549/29; 549/62; 549/78
(58) Field of Search ................ 546/309, 314, 546/334, 339; 514/352, 357, 354, 277, 438, 445; 549/29, 62, 78

(56) References Cited

FOREIGN PATENT DOCUMENTS

| EP | 0 776 881 | 6/1997 |
| EP | 0 850 909 | 7/1998 |
| WO | WO 00/26167 | 5/2000 |

*Primary Examiner*—Zinna Northington Davis
(74) *Attorney, Agent, or Firm*—Burns, Doane, Swecker & Mathis, L.L.P.

(57) ABSTRACT

The invention relates to novel bicyclic compounds having the general formula (I):

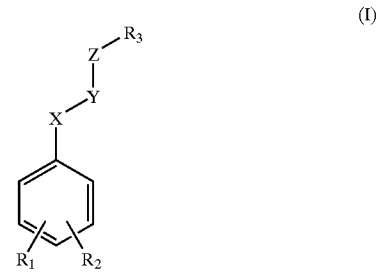

as well as to a method for preparing them and to their use in pharmaceutical compositions intended for use in human or veterinary medicine (in dermatology, in carcinology and in the field of autoimmune diseases and that of organ or tissue transplants in particular), or alternatively in cosmetic compositions.

14 Claims, No Drawings

VITAMIN D ANALOGUES

The invention relates, as novel and useful industrial products, to biaromatic compounds which are vitamin D analogues. The invention also relates to a process for preparing them and to their use in pharmaceutical compositions intended for use in human or veterinary medicine, or alternatively in cosmetic compositions.

The compounds according to the invention have pronounced activity in the fields of cell proliferation and differentiation and find applications more particularly in the topical and systemic treatment of dermatological (or other) complaints associated with a keratinization disorder, complaints with an inflammatory and/or immunoallergic component and hyperproliferation of tissues of ectodermal origin (skin, epithelium, etc.), whether benign or malignant. These compounds can also be used to combat ageing or the skin, whether light-induced or chronological, and to treat cicatrization disorders.

The compounds according to the invention can also be used in cosmetic compositions for body and hair hygiene.

Vitamin D is an essential vitamin for preventing and treating mineralization defects of cartilage (rickets) and of bone (osteomalacia), and even of certain forms of osteoporosis in elderly people. However, it is now accepted that its functions extend well beyond regulating bone metabolism and calcium homeostasis. Among these functions, mention may be made of its action on cell proliferation and differentiation and the control of the immune defences. Their discovery has opened the way to novel therapeutic approaches in dermatology, carcinology and in the field of autoimmune diseases and that of organ or tissue transplants.

An efficient therapeutic supply has long been confounded by the toxicity of this vitamin (occasionally fatal hypercalcaemia). Structural analogues of vitamin D are currently synthesized, some of which conserve only the differentiating properties and have no action on calcium metabolism.

One of the aims of the present invention is to propose novel compounds which are structural analogues of vitamin D and which show selective activity on cell proliferation and differentiation without displaying any hypercalcaemiant nature.

Another aim of the present invention is to propose novel compounds which are analogues of vitamin D and which are more readily synthesized and thus more economical than those known previously.

Thus, the present invention relates to compounds which can be represented by the general formula (I) below:

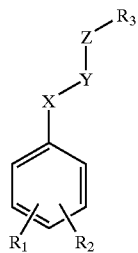

(I)

in which:
  $R_1$ represents a hydrogen atom, a $CH_3$ radical or a radical $-(CH_2)_s-OR_4$,
  $R_2$ represents a radical $-(CH_2)_t-OR_5$, s, t, $R_4$ and $R_5$ having the meanings given below, X—Y represents a bonding group chosen from the bonding groups of formulae (a) to (i) below:

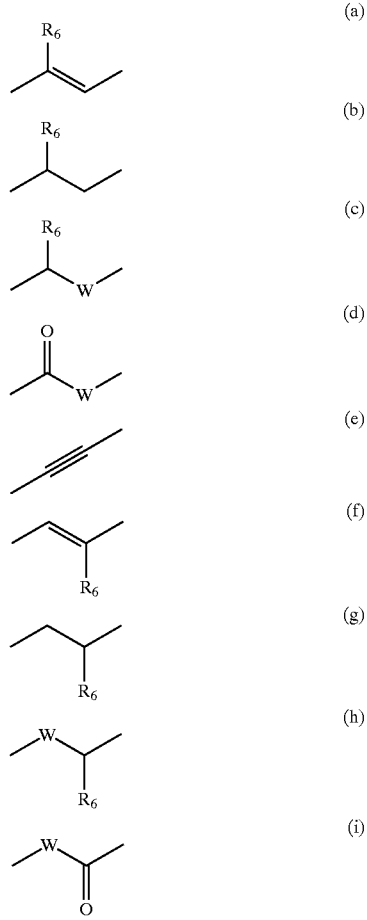

$R_6$ and W having the meanings given below,

Z represents a ring chosen from the rings of formulae (j) to (n) below:

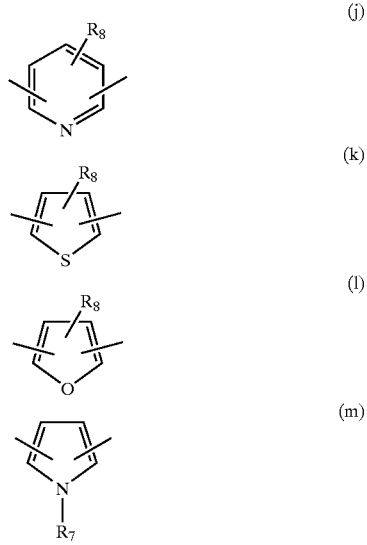

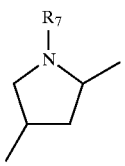 (n)

R7 and R8 having the meanings given below, it being understood that when Z represents the rings of formula (k), (l) or (m), then X—Y cannot represent a bonding group of formula (c) or (d), it being understood that when Z represents a ring of formula (n), then X—Y preferably represents a bonding group of formula (c) or (d), $R_3$ represents an alkyl chain containing from 4 to 8 carbon atoms substituted with one or more hydroxyl groups, it being possible for the hydroxyl groups to be protected in the form of acetoxy, methoxy or ethoxy, trimethylsilyloxy, tert-butyldimethylsilyloxy, tetrahydropyranyloxy and optionally also:

substituted with one or more lower alkyl or cycloalkyl groups and/or substituted with one or more halogen atoms and/or substituted with one or more $CF_3$ groups and/or in which one or more carbon atoms of the chain are replaced with oxygen, sulphur or nitrogen atoms, it being possible for the nitrogen atoms to be optionally substituted with lower alkyl radicals and/or in which one or more single bonds of the chain are replaced with one or more double and/or triple bonds, $R_3$ being positioned on the ring para or meta to the bonding group X—Y, s and t, which may be identical or different, being 1 or 2, $R_4$ and $R_5$, which may be identical or different, represent a hydrogen atom, an acetyl radical, a benzoyl radical, a trimethylsilyl radical, a tert-butyldimethylsilyl radical or a tetrahydropyranyl radical, $R_6$ represents a hydrogen atom or a lower alkyl radical, W represents an oxygen or sulphur atom or an —NH— radical which can optionally be substituted with a lower alkyl radical, $R_7$ represents a hydrogen atom or a lower alkyl radical, $R_8$ represents a hydrogen atom, a lower alkyl radical or a halogen atom.

The invention is also directed towards the optical and geometrical isomers of the said compounds of formula (I), as well as towards the salts thereof when X—Y represent a bonding group of formulae (c) and (h) and W represents an —NH— radical optionally substituted with a lower alkyl radical.

When the compounds according to the invention are in the form of salts, they are pharmaceutically or cosmetically acceptable salts obtained by addition of an inorganic or organic acid, in particular hydrochloric acid, sulphuric acid, acetic acid, fumaric acid, hemisuccinic acid, maleic acid or mandelic acid.

According to the present invention, the expression "lower alkyl radical" means a linear or branched radical containing from 1 to 6 carbon atoms, and preferably methyl, ethyl, isopropyl, tert-butyl and hexyl radicals.

The expression "cycloalkyl radical" means a cyclic or polycyclic alkane radical containing from 3 to 10 carbon atoms. The cycloalkyl radical is preferably chosen from a cyclopropyl, cyclopentyl or cyclohexyl radical.

The expression "halogen atom" preferably means a fluorine, chlorine or bromine atom.

Among the compounds of formula (I) falling within the context of the present invention, mention may be made in particular of the following:

(E)-7-[5-(3,4-bis-hydroxymethyl-phenoxymethyl)-2-thienyl]-3-ethyloct-6-en-3-ol (E)-7-[4-(3,4-bis-hydroxymethyl-phenoxymethyl)-2-thienyl]-3-ethyloct-6-en-3-ol (E)-7-[2-(3,4-bis-hydroxymethyl-phenoxymethyl)-4-thienyl]-3-ethyloct-6-en-3-ol (E)-7-[5-(3,4-bis-hydroxymethyl-phenoxymethyl)-3-pyridyl]-3-ethyloct-6-en-3-ol (E)-7-[6-(3,4-bis-hydroxymethyl-phenoxymethyl)-2-pyridyl]-3-ethylnon-6-en-3-ol (E)-7-[5-(3,4-bis-hydroxymethyl-phenoxymethyl)-2-thienyl]-3-ethylnon-6-en-3-ol (4E,6E)-7-[5-(3,4-bis-hydroxymethyl-phenoxymethyl)-2-thienyl]-3-ethylnona-4,6-dien-3-ol (3E,5E)-6-[5-(3,4-bis-hydroxymethyl-phenoxymethyl)-2-thienyl]-1,1,1-trifluoro-2-trifluoromethylocta-3,5-dien-2-ol (4E,6E)-7-[5-(3,4-bis-hydroxymethyl-phenoxymethyl)-2-thienyl]-1,1,1,2,2-pentafluoro-3-pentafluoroethylnona-4,6-dien-3-ol (E)-7-[5-(3,4-bis-hydroxymethyl-phenoxymethyl)-3-thienyl]-3-ethyl-4,4-dimethylnon-6-en-3-ol (E)-7-{5-[2-(3,4-bis-hydroxymethyl-phenyl)ethyl]-2-thienyl}-3-ethylnon-6-en-3-ol (4E,6E)-7-{5-[2-(3,4-bis-hydroxymethyl-phenyl)ethyl]-2-thienyl}-3-ethylnona-4,6-dien-3-ol (3E,5E)-6-{5-[2-(3,4-bis-hydroxymethyl-phenyl)ethyl]-2-thienyl}-1,1,1-trifluoro-2-trifluoromethylocta-3,5-dien-2-ol ((4E,6E)-7-{5-[2-(3,4-bis-hydroxymethyl-phenyl)ethyl]-2-thienyl}-1,1,1,2,2-pentafluoro-3-pentafluoroethylnona-4,6-dien-3-ol (4E,6E)-7-[5-(3,4-bis-hydroxymethyl-benzylamino)-2-thienyl]-3-ethylnona-4,6-dien-3-ol (4E,6E)-7-{5-[(3,4-bis-hydroxymethyl-benzyl)methylamino]-2-thienyl}-3-ethylnona-4,6-dien-3-ol (4E,6E)-7-{5-[(3,4-bis-hydroxymethyl-benzyl)propylamino]-2-thienyl}-3-ethylnona-4,6-dien-3-ol (E)-7-[4-(3,4-bis-hydroxymethyl-phenoxymethyl)-2-thienyl]-3-ethylnon-6-en-3-ol (4E,6E)-7-[4-(3,4-bis-hydroxymethyl-phenoxymethyl)-2-thienyl]-3-ethylnona-4,6-dien-3-ol (3E,5E)-6-[4-(3,4-bis-hydroxymethyl-phenoxymethyl)-2-thienyl]-1,1,1-trifluoro-2-trifluoromethylocta-3,5-dien-2-ol (E)-7-{4-[2-(3,4-bis-hydroxymethyl-phenyl)ethyl]-2-thienyl}-3-ethylnon-6-en-3-ol (4E,6E)-7-{4-[2-(3,4-bis-hydroxymethyl-phenyl)ethyl]-2-thienyl}-3-ethylnona-4,6-dien-3-ol (3E,5E)-6-{4-[2-(3,4-bis-hydroxymethyl-phenyl)ethyl]-2-thienyl}-1,1,1-trifluoro-2-trifluoromethylocta-3,5-dien-2-ol (E)-7-[5-(3,4-bis-hydroxymethyl-phenoxymethyl)-3-thienyl]-3-ethylnon-6-en-3-ol (4E,6E)-7-[5-(3,4-bis-hydroxymethyl-phenoxymethyl)-3-thienyl]-3-ethylnona-4,6-dien-3-ol (3E,5E)-6-[5-(3,4-bis-hydroxymethyl-phenoxymethyl)-3-thienyl]-1,1,1-trifluoro-2-trifluoromethylocta-3,5-dien-2-ol (E)-7-{5-[2-(3,4-bis-hydroxymethyl-phenyl)ethyl]-3-thienyl}-3-ethylnon-6-en-3-ol (4E,6E)-7-{5-[2-(3,4-bis-hydroxymethyl-phenyl)ethyl]-3-thienyl}-3-ethylnona-4,6-dien-3-ol (3E,5E)-6-{5-[2-(3,4-bis-hydroxymethyl-phenyl)ethyl]-3-thienyl}-1,1,1-trifluoro-2-trifluoromethylocta-3,5-dien-2-ol.

According to the present invention, the compounds of formula (I) that are more particularly preferred are those for which at least one, and preferably all, of the following conditions are satisfied:

$R_1$ represents a —$CH_3$ or —$(CH_2)_sOH$ radical, $R_2$ represents a radical —$(CH_2)_tOH$, X—Y represents a bonding group of formula (b), (c), (h) or (g), $R_3$ is chosen from
- an alkyl or alkenyl chain of 4 to 8 carbon atoms substituted with at least one hydroxyl radical and at least one lower alkyl radical,
- or an alkyl or alkenyl chain of 4 to 8 carbon atoms substituted with at least one hydroxyl radical, at least one lower alkyl radical and at least one $CF_3$ radical.

A subject of the present invention is also processes for preparing the compounds of formula (I).

FIGS. 1 to 6 represent reaction schemes which can be carried out to prepare the compounds according to the invention.

Thus, the compounds of formula I(a) can be obtained (FIG. 1) by reacting a halo compound, preferably a bromo compound, (1) with a phenolic (Y=OH), thiophenolic (Y=SH) or aniline (Y=NH—COO-tert-butyl) derivative (3) in the presence of a base such as $K_2CO_3$ in a solvent such as acetone or methyl ethyl ketone.

The compounds of formula I(a) can also be obtained (FIG. 1) by reacting a halo compound, preferably a bromo compound, (1) with the sodium or potassium salt of a phenolic (Y=OH), thiophenolic (Y=SH) or aniline (Y=NH—COO-tert-butyl) derivative (3) in a solvent such as dimethylformamide (DMF).

The compounds of formula I(b) can be obtained (FIG. 1) by reacting a benzoic derivative (2) with a phenolic (Y=OH), thiophenolic (Y=SH) or aniline (Y=$NH_2$) derivative (3) in the presence of carbonyldiimidazole or dicyclohexylcarbodiimide in a solvent such as dichloromethane or tetrahydrofuran (THF).

The compounds of formula I(b) can also be obtained (FIG. 1) by reacting a benzoyl chloride (obtained by reacting a benzoic derivative (2) with thionyl chloride or oxalyl chloride) with a phenolic (Y=OH), thiophenolic (Y=SH) or aniline (Y=$NH_2$) derivative (3) in the presence of a base such as triethylamine in a solvent such as dichloromethane or tetrahydrofuran (THF).

The compounds (1) and (2) can be obtained according to the reaction schemes given in FIGS. 2 and 3. These methods for preparing the compounds (1) and (2) have the advantage of limiting the number of preparation steps.

In FIG. 2, (a) represents a reaction with $BF_3$ in dioxane, (b) represents a reaction with $CH_3OCH_2Cl$ in the presence of sodium hydride in a dimethylformamide solvent, (c) represents a reaction with n-butyllithium in the presence of $CO_2$ in a solvent such as tetrahydrofuran, (d) represents a reaction with n-butyllithium in tetrahydrofuran followed by a reaction with dimethylformamide, (e) represents a reduction reaction with sodium borohydride in a methanol-tetrahydrofuran solvent and (f) represents a reaction with carbon tetrabromide in the presence of triphenylphosphine in a dichloromethane solvent.

In FIG. 3, (a) represents a reaction with $BH_3$ in dioxane, (b) represents a reaction with methanol in the presence of sulphuric acid, (c) represents a reaction with t-$C_4H_9(CH_3)_2$SiCl in the presence of imidazole in a dimethylformamide solvent, (d) represents a reaction with $LiAlH_4$ in ether, (e) represents a reaction with benzoyl chloride in the presence of triethylamine in a solvent such as tetrahydrofuran, (f) represents a reaction with $(C_4H_9)_4NF$ in a solvent such as tetrahydrofuran and (g) represents a reaction with carbon tetrabromide in the presence of triphenylphosphine in a dichloromethane solvent.

The compounds of formula I(c) can be obtained (FIG. 4) by a Horner-Emmons reaction between the phosphonate derivative (7) (obtained from the corresponding benzyl bromide by an Arbuzov reaction) and the aldehyde derivative (6). The derivative (6) can be obtained from the bromo ketone derivative (4), first by protecting the ketone function in the form of dioxolane (5) and then by forming the lithium derivative and reaction with dimethylformamide.

The compounds of formula I(d) can be obtained from the compounds (8) by hydrogenation of the double bond in the presence of palladium-on-charcoal.

The compounds of formula I(c) can also be obtained (FIG. 5) by a Heck reaction between an ethylenic derivative (13) (obtained by reaction of the benzaldehyde (12) with methyltriphenylphosphonium bromide) and the triflate (X=$OSO_2CF_3$) or iodo (X=I) derivative (15) in the presence of a transition metal catalyst such as $Pd(Cl)_2(PPh_3)_2$ in a solvent such as triethylamine.

The compounds of formula I(e) can be obtained (FIG. 5) by a Sonogashira reaction between an acetylenic derivative (14) (obtained from the benzaldehyde (12) by a Corey-Fuchs reaction) and a triflate derivative (X=$OSO_2CF_3$) or iodo derivative (X=I) (15) in the presence of a transition metal catalyst such as $Pd(Cl)_2(PPh_3)_2$ and CuI in a solvent such as triethylamine.

The chain $R_3$ can be introduced using, for example, the methods described in Medicinal Research Reviews, Vol. 7, No. 2, 147–171 (1987) T. KAMETANI and H. FURUYAMA, Chem. Rev. Vol. 78, No. 3, 199–241 (1978) D. M. PIATAK and J. WICHA, or in Chem. Rev. Vol. 95, No. 6, 1877–1952 (1995) G. ZHU and W. H. OKAMURA.

Thus, as examples, a few summarized methods are given in FIG. 6 in which (a) represents a reaction with MgBr—$CH_2$—$(CH_2)_n$—$C(CH_3)_2$—O-tetrahydropyran in a solvent such as tetrahydrofuran, (b) represents a reaction in the presence of para-toluenesulphonic acid or sulphuric acid, (c) represents a hydrogenation reaction in the presence of a catalyst such as palladium-on-charcoal, (d) represents a reduction reaction with sodium borohydride in a methanol-tetrahydrofuran solvent, (e) represents a reaction with Br—$CH_2$—$(CH_2)_n$—$CH_2$—COOR in the presence of potassium hydride in a dimethylformamide solvent, (f) represents a reaction with MgXAlkyl, X representing a halogen atom, in a solvent such as tetrahydrofuran, (g) represents a reaction with NC—$CH_2$—P(O) $(OC_2H_5)_2$ in the presence of sodium hydride in a solvent such as tetrahydrofuran, (h) represents a reaction with diisobutylaluminium hydride in a solvent such as tetrahydrofuran, (i) represents a reaction with carbon tetrabromide in the presence of triphenylphosphine in a solvent such as tetrahydrofuran followed by a reaction with n-butyllithium, (j) represents a reaction with n-butyllithium in a solvent such as tetrahydrofuran, (k) represents a reaction with the alkyl chloroformate Cl—COOR, (l) represents a reaction with MgXAlkyl, X representing a halogen atom, in a solvent such as tetrahydrofuran, (m) represents a reaction with n-butyllithium in a solvent such as tetrahydrofuran, (n)

represents a reaction with CF$_3$—CO—CF$_3$, (0) represents a reaction with HOOC—(CH$_2$)$_3$—P(C$_6$H$_5$)$_3$Br in the presence of potassium tert-butoxide in a solvent such as tetrahydrofuran, (p) represents a reaction with ethanol in the presence of sulphuric acid, (q) represents a reaction with MgXAlkyl, X representing a halogen atom, in a solvent such as tetrahydrofuran, (r) represents a reaction with ROOC—CH=CH—CH$_2$—P(O) (OC$_2$H$_5$)$_2$ in the presence of lithium diisopropylamide in a solvent such as tetrahydrofuran, and (s) represents a reaction with an alkyllithium derivative in a solvent such as tetrahydrofuran.

The compounds of general formula (I) have biological properties analogous to those of vitamin D, in particular the properties of transactivation of the vitamin D response elements (VDRE), such as an agonist or antagonist activity with respect to receptors of vitamin D or derivatives thereof. The expression "D vitamins or derivatives thereof" means, for example, the derivatives of vitamin D$_2$ or D3 and in particular 1,25-dihydroxyvitamin D$_3$ (calcitriol).

This agonist activity with respect to receptors of vitamin D or derivatives thereof can be demonstrated "in vitro" by methods known in the field of study of gene transcription (Hansen et al., The Society for Investigative Dermatology, vol. 1, No. 1, April 1996).

By way of example, the VDR agonist activity can be tested on the HeLa cell line by co-transfection with an expression vector for the human VDR receptor and the reporter plasmid p240Hase-CAT which contains the region −1399 to +76 of rat 24-hydroxylase promoter, cloned upstream of the frame encoding the chloramphenicol-acetyl-transferase (CAT) gene. 18 hours after co-transfection, the test product is added to the medium. After treatment for 18 hours, assay of the CAT activity in the cell lysates is carried out by an ELISA test. The results are expressed as percentages of the effect normally observed with $10^{-7}$M calcitriol.

The agonist activity can also be characterized in the co-transfection system, by determining the dose required to reach 50% of the maximum activity of the product (AC50).

The biological properties of the vitamin D analogues can also be measured by the capacity of the product to inhibit the proliferation of normal human keratinocytes (NHK in culture). The product is added to NHKs cultured under conditions which promote the proliferative state. The product is left in contact with the cells for 5 days. The number of proliferative cells is measured by incorporation of bromodeoxyuridine (BRdU) into the DNA.

The vitamin D receptor agonist activity of the compounds of the invention can also be evaluated "in vivo" by induction of 24-hydroxylase in SKH mice. (Voorhees et al., 1997.108: 513–518).

A subject of the present invention is also, as medicinal products, the compounds of formula (I) as described above.

The compounds according to the invention are particularly suitable in the following fields of treatment:

1) for treating dermatological complaints associated with a keratinization disorder which has a bearing on differentiation and on proliferation, in particular for treating simple acne, comedones, polymorphonuclear leukocytes, rosacea, nodulocystic acne, acne conglobata, senile acne and secondary acnes such as solar, medication-related or professional acne,
2) for treating other types of keratinization disorders, in particular ichthyosis, ichthyosiform states, Darier's disease, palmoplantar keratoderma, leukoplasias and leukoplasiform states, and cutaneous or mucous (buccal) lichen,
3) for treating other dermatological complaints with an inflammatory and/or immunoallergic component, with or without cell proliferation disorders, and, in particular, all forms of psoriasis, whether this is cutaneous, mucous or ungual psoriasis, and even psoriatic rheumatism, or alternatively cutaneous atopy, such as eczema or respiratory atopy or alternatively gingival hypertrophy,
4) for treating all dermal or epidermal proliferations, whether benign or malignant and whether they are of viral origin or otherwise, such as common warts, flat warts and verruciform epidermodysplasia, oral or florid papillomatoses, T lymphoma and proliferations which may be induced by ultraviolet radiation, in particular in the case of basocellular and spinocellular epithelioma, as well as any pre-cancerous skin lesion such as keratoacanthomas,
5) for treating other dermatological disorders such as immune dermatitis such as lupus erythematosus, immune bullosis and collagen diseases such as scleroderma,
6) in the treatment of dermatological or general complaints with an immunological component,
7) for combating disorders of sebaceous function such the hyperseborrhoea of acne or simple seborrhoea,
8) in the treatment of skin disorders due to exposure to UV radiation, as well as for preparing or combating ageing of the skin, whether it is light-induced or chronological ageing, or for reducing actinic keratoses and pigmentations, or any pathologies associated with chronological or actinic ageing,
9) for preventing or treating cicatrization disorders or for preventing or repairing stretchmarks,
10) in the treatment of inflammatory complaints such as arthritis,
11) in the treatment of any complaint of viral origin on the skin or generally, such as Kaposi's syndrome,
12) for treating certain ophthalmological disorders, in particular corneopathies,
13) in the treatment of prevention of cancerous or pre-cancerous states of cancers presenting or possibly being induced by vitamin D receptors, such as, but without limitation, breast cancer, leukaemia, myelodysplasic syndromes and lymphomas, carcinomas of the Malpighian epithelial cells and gastrointestinal cancers, melanomas and osteosarcoma,
14) in the prevention or treatment of alopecia of various origins, in particular alopecia due to chemotherapy or radiation,
15) in the treatment of immune system complaints, such as autoimmune diseases, for instance type 1 diabetes mellitus, multiple sclerosis, lupus and lupus-type complaints, asthma, glomerulonephritis, selective dysfunctions of the immune system such as AIDS, or prevention of immune rejection such as kidney, heart, bone marrow, liver, pancreatic islet, pancreas or skin graft rejection, or prevention of graft-versus-host disease,
16) in the treatment of endocrine complaints, given that the vitamin D analogues can modify hormonal secretion such as increasing the secretion of insulin or selectively suppressing the secretion of parathyroid hormone, for example in chronic renal insufficiency and secondary hyperparathyroidism,
17) in the treatment of complaints characterized by abnormal management of intracellular calcium, and in the treatment or prevention of pathologies in which calcium metabolism is involved, such as muscular ischaemia (myocardial infarction), 18) in the treatment or prevention of vitamin D deficiencies and other mineral homeostasis complaints in plasma and bone, such as rickets, osteomalacia, osteoporosis, in particular in the case of menopausal women, renal osteodystrophy and parathyroid function disorders, 19) in the treatment of complaints of the cardiovascular system such as arteriosclerosis or hypertension, as well as non-insulin-dependent diabetes.

In the therapeutic fields mentioned above, the compounds according to the invention can advantageously be used in combination with retinoids, with corticosteroids or oestrogens, in combination with antioxidants, with α-hydroxy or α-keto acids or derivatives thereof, with potassium-channel blockers, or alternatively in combination with other medicinal products known to interfere with the immune system (for example cyclosporin, FK 506, glucocorticoids, monoclonal antibodies, cytokines or growth factors, etc.).

The term "retinoids" means either natural or synthetic RAR- or RXR-receptor ligands.

The expression "free-radical scavengers" means, for example, α-tocopherol, superoxide dismutase, ubiquinol or certain metal-chelating agents.

The expression "α-hydroxy or α-keto acids or derivatives thereof" means, for example, lactic acid, malic acid, citric acid, glycolic acid, mandelic acid, tartaric acid, glyceric acid, ascorbic acid and salicylic acid derivatives, as well as salts, amides or esters thereof.

The expression "potassium-channel blockers" means, for example, Minoxidil (2,4-diamino-6-piperidinopyrimidine 3-oxide) and derivatives thereof.

A subject of the present invention is also a pharmaceutical composition comprising at least one compound of formula (I) as defined above.

A subject of the present invention is thus also such a pharmaceutical composition intended in particular for treating the abovementioned complaints.

The compounds according to the invention can be administered via the enteral, parenteral, topical or ocular route.

Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions can be in the form of solutions or suspensions for infusion or for injection. The compounds according to the invention are generally administered at a daily dose of about from 0.001 µg/kg to 1000 µg/kg and preferably of about from 0.01 µg/kg to 100 µg/kg of bodyweight in 1 to 3 dosage intakes.

Via the topical route, the pharmaceutical compositions based on compounds according to the invention are intended for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication.

Via the ocular route, they are mainly eye drops.

These topical-route or ocular-route compositions contain at least one compound of formula (I) as defined above at a concentration preferably of between 0.0001% and 5% and preferably between 0.001% and 1% relative to the total weight of the composition.

The compounds of formula (I) according to the invention also find an application in the cosmetics field, in particular in body and hair hygiene and especially for treating skin with a tendency towards acne, for regrowth of the hair, for preventing hair loss, for combating the greasy appearance of the skin or the hair, in protecting against the harmful effects of sunlight or in treating physiologically dry skin, for preventing and/or combating light-induced or chronological ageing.

In the cosmetics field, the compounds according to the invention can advantageously be used in combination with retinoids, with corticosteroids, in combination with free-radical scavengers, with α-hydroxy or α-keto acids or derivatives thereof, or alternatively with ion-channel blockers, the various products taken in combination with the compounds of the present invention being as defined above.

The present invention is thus also directed towards a cosmetic composition containing, in a cosmetically acceptable support, at least one compound of formula I as defined above. This cosmetic composition can be in particular in the form of a cream, a milk, a lotion, a gel, microspheres or nanospheres or lipid vesicles or polymer vesicles, a soap or a shampoo.

The concentration of compound of formula I in the cosmetic compositions can be between 0.001% and 3% by weight relative to the total weight of the composition.

The pharmaceutical and cosmetic compositions according to the invention can also contain inert or even pharmacodynamically or cosmetically active additives or combinations of these additives and, in particular: wetting agents; depigmenting agents such as hydroquinone, azaleic acid, caffeic acid or kojic acids; emollients; moisturizing agents such as glycerol, PEG 400, thiamorpholinone and derivatives thereof or urea; antiseborrhoeic or antiacne agents, such as S-carboxymethylcysteine or S-benzylcysteamine and salts and derivatives thereof, or benzoyl peroxide; antibiotics such as erythromycin and esters thereof, neomycin, clindamycin and esters thereof, tetracyclines; antifungal agents such as ketoconazole or poly-4,5-methylene-3-isothiazolinones; agents for promoting regrowth of the hair, such as Minoxidil (2,4-diamino-6-piperidinopyrimidine 3-oxide) and derivatives thereof, Diazoxide (7-chloro-3-methyl-1,2,4-benzothiadiazine 1,1-dioxide) and Phenytoin (5,4-diphenylimidazolidine-2,4-dione); non-steroidal anti-inflammatory agents; carotenoids, and in particular β-carotene; anti-psoriatic agents such as anthralin and derivatives thereof, and, finally, eicosa-5,8,11,14-tetraynoic acid and eicosa-5,8,11-triynoic acid, and esters and amides thereof.

The compositions according to the invention can also contain flavour enhancers, preserving agents such as para-hydroxybenzoic acid esters, stabilizers, moisture regulators, pH regulators, osmotic pressure modifiers, emulsifiers, UV-A and UV-B screening agents, antioxidants such as α-tocopherol, butylhydroxyanisole or butylhydroxytoluene.

Several examples of the production of active compounds of formula (I) according to the invention, and several concrete formulations based on such compounds, and an example of a test for evaluating the biological activity of compounds of formula (I) according to the invention, will now be given by way of illustration and with no limiting nature.

EXAMPLE 1

(E)-7-[5-(3,4-bis-Hydroxymethyl-phenoxymethyl)-2-thienyl]-3-ethyloct-6-en-3-ol a) 4-Aminophthalic Acid 1 g (4.73 mmol) of 4-nitrophthalic acid is dissolved in 10 mL of anhydrous ethanol. The solution is stirred at room temperature and degassed under argon. 50 mg of palladium/charcoal (5%) are added in a single portion and hydrogen is bubbled into the solution. After 3 hours, the solution is filtered through Celite and then evaporated.

Orange-coloured oil. m=820 mg. Y=96%. $^1$H NMR (DMSO): 3.32 (1H, s), 5.95 (1H, s), 6.49–6.53 (2H, m), 7.46–7.50 (1H, d, J=8.8 Hz), 12.33 (2H, COOH, s).

b) Methyl 4-Hydroxyphthalate

A solution of 5 g (27.6 mmol) of 4-aminophthalic acid in 50 mL of sulphuric acid (1 M) is cooled to 0° C. A solution of 2.27 g of sodium nitrite in 6 mL of water is then added slowly. After 15 minutes at 0° C., 15 mL of concentrated sulphuric acid are added and the mixture is maintained at 100° C. with vigorous stirring for 1 hour. At room temperature, the reaction medium is extracted with ethyl acetate and washed with water. After separation of the phases by settling, the organic phase is dried over magnesium sulphate and concentrated. The residue is purified on a column of silica (80 dichloromethane/20 methanol). It is then dissolved in 100 mL of methanol and refluxed with 2 mL of sulphuric acid. After disappearance of the diacid, the methanol is evaporated off and the product is taken up in ethyl acetate and washed with water. The organic phase is separated out after settling, dried over sodium sulphate and evaporated.

M=5.2 g. Y=90%. $^1$H NMR (DMSO): 3.64 (3H, s), 3.67 (3H, s), 6.79–6.86 (2H, m), 7.56–7.60 (1H, d, J=8.4 Hz), 10.51 (1H, OH, s).

c) Ethyl (E)-5-(Bromo-2-thienyl)-4-hexenoate 22.2 g (51.7 mmol) of (3-carboxypropyl)triphenylphosphonium bromide are dried under vacuum for 1 h with heating at 130° C., and then cooled to room temperature and dissolved in 200 mL of anhydrous THF. 11.5 g (102.5 mmol) of potassium tert-butoxide in 100 mL of THF are then added slowly, after which the orange-red mixture is stirred for 15 minutes. A solution of 7 g (34 mmol) of 1-(5-bromo-2-thienyl)ethanone in 100 mL of THF is then added dropwise and the reaction medium is stirred for 15 hours. After treatment with saturated ammonium chloride solution, extraction with ethyl acetate, drying and evaporation of the solvents from the organic phase, the residue obtained is purified by chromatography on a column of silica. An ochre-coloured solid is obtained (m.p.: 62–64° C., m=5.8 g; Y=62%). This product is then dissolved in 100 mL of ethanol and 2 mL of sulphuric acid are then added. The reaction medium is brought to reflux and stirred for 2 hours. After treatment with water, the medium is extracted with ethyl acetate and the organic phases are then combined, dried and concentrated under reduced pressure. The residue obtained is purified by chromatography on a column of silica (eluent: 95 heptane/5 ethyl acetate) to give the pure trans isomer in the form of a yellow oil (m=3.4 g; Y=77%).

d) (E)-7-(5-Bromo-2-thienyl)-3-ethyloct-6-en-3-ol 3.3 g of ethyl (E)-5-(5-bromo-2-thienyl)-4-hexenoate (10.9 mmol) are dissolved in 50 mL of ethyl ether. 22 mL of 2.0 M ethylmagnesium chloride solution (44 mmol) are then added dropwise and the reaction medium is stirred at room temperature for 30 minutes. After treatment with saturated ammonium chloride solution, extraction with ethyl ether and then drying and evaporation of the solvents from the organic phase, the residue obtained is purified by chromatography on a column of silica. A colourless oil is obtained (m=2.4 g; Y=70%).

e) [(E)-5-(5-Bromo-2-thienyl)-1,1-diethylhex-4-enyloxy]triethylsilane 2.2 g (6.9 mmol) of (E)-7-(5-bromo-2-thienyl)-3-ethyloct-6-en-3-ol are dissolved in 50 mL of dichloromethane. 25 mg (0.2 mmol) of 4-dimethylaminopyridine and 4.8 mL of triethylamine (34.8 mmol) are added and the reaction medium is cooled to 0° C. 3.9 mL (17.4 mmol) of triethylsilyl trifluoromethanesulphonate are added dropwise. After the addition, the reaction medium is warmed to room temperature and then treated with water and extracted with dichloromethane. After separation of the phases by settling, drying and concentration of the organic phases under reduced pressure, the residue obtained is purified by chromatography on a column of silica. A yellow oil is obtained (m=2.3 g; Y=97%).

f) [5-((E)-5-Ethyl-1-methyl-5-triethylsilanyloxyhept-1-enyl)-2-thienyl]methanol 2.8 g (6.5 mmol) of [(E)-5-(5-bromo-2-thienyl)-1,1-diethylhex-4-enyloxy]triethylsilane are dissolved in 50 mL of anhydrous THF and the mixture is then cooled to –78° C. 2.9 mL (7.1 mmol) of 2.5 M butyllithium solution are then added, after which the reaction medium is stirred for 15 minutes. 0.55 mL of anhydrous DMF is then added, after which the reaction medium is warmed to room temperature and stirred for 1 h. After treatment with saturated ammonium chloride solution and then extraction with ethyl acetate, the organic phases are combined, dried and concentrated under reduced pressure. The residue containing the desired 5-((E)-5-ethyl-1-methyl-5-triethylsilanyloxyhept-1-enyl)thiophene-2-carbaldehyde is then dissolved in 50 mL of anhydrous methanol, after which 150 mg (3.9 mmol) of sodium borohydride are added in two portions. After stirring for 10 minutes, the medium is treated with ammonium chloride solution and extracted with ethyl ether. The organic phases are combined, dried and concentrated under reduced pressure. After purification by chromatography on a column of silica, a yellow oil is obtained (m=1.76 g; Y=71%).

g) Dimethyl 4-[5-((E)-5-Ethyl-1-methyl-5-triethylsilanyloxyhept-1-enyl)-2-thienylmethoxy]phthalate 1 g (2.6 mmol) of [5-((E)-5-ethyl-1-methyl-5-triethylsilanyloxyhept-1-enyl)-2-thienyl]methanol is dissolved in 50 mL of dichloromethane and cooled to 0° C. 0.55 mL (3.9 mmol) of triethylamine is added, followed by 220 mL of methylsulphonyl chloride (2.9 mmol). After stirring for 20 minutes, the reaction medium is treated with ammonium chloride solution and extracted with dichloromethane. The organic phases are combined, dried and concentrated under reduced pressure. The residue obtained is then purified by chromatography on a column of silica to yield the desired product.

h) Dimethyl 4-[5-((E)-5-Ethyl-5-hydroxy-1-methylhept-1-enyl)-2-thienylmethoxy]phthalate 750 mg (1.3 mmol) of dimethyl 4-[5-((E)-5-ethyl-1-methyl-5-triethylsilanyloxyhept-1-enyl)-2-thienylmethoxy]phthalate are dissolved in 30 mL of THF. 2.6 mL (2.6 mmol) of a 1.0 M tetrabutylammonium fluoride solution are added and the reaction medium is heated at 60° C. for 3 hours. After treatment with ammonium chloride solution and extraction with ethyl acetate, the organic phases are combined, dried and concentrated under reduced pressure. The residue is purified by chromatography on a column of silica. A yellow oil is obtained (m=355 mg; Y=59%).

i) (E)-7-[5-(3,4-bis-Hydroxymethyl-phenoxymethyl)-2-thienyl]-3-ethyloct-6-en-3-ol 350 mg (0.76 mmol) of dimethyl 4-[5-((E)-5-ethyl-5-hydroxy-1-methylhept-1-enyl)-2-thienylmethoxy]phthalate are dissolved in 20 mL of anhydrous ethyl ether. 70 mg (1.8 mmol) of lithium aluminium hydride are added and the reaction medium is stirred at room temperature for 30 minutes. 400 mL of water are then added slowly and the medium is filtered. The filtrate is concentrated under reduced pressure and the residue obtained is then purified by chromatography on a column of silica (eluent: 70 ethyl acetate/ 30 heptane). A white solid (m.p.: 100–102° C.) is obtained (m=175 mg; Y=58%).

$^1$H NMR (DMSO): 0.82 (t, 6H, J=7.3 Hz), 1.42 (q, 4H, J=7.4 Hz), 2.03 (s, 3H), 2.1–2.25 (m, 2H), 3.97 (s, 1H), 4.49 (d, 2H, J=5.3 Hz), 4.58 (d, 2H, J=5. 3 Hz), 5.00 (t, 1H), 5.17 (t, 1H), 5.26 (s, 2H), 5.92 (t, 1H), 6.90–6.97 (m, 2H), 7.10 (m, 2H), 7.3 (m, 2H).

EXAMPLE 2

(E)-7-[4-(3,4-bis-Hydroxymethyl-phenoxymethyl)-2-thienyl]-3-ethyloct-6-en-3-ol a) Ethyl (E)-5-(4-Bromo-2-thienyl)-4-hexenoate In a manner similar to that of Example 1(c), by reaction of 18.8 g (43.9 mmol) of (3-carboxypropyl) triphenylphosphonium bromide with 6 g (29.2 mmol) of 1-(4-bromo-2-thienyl)ethanone, 6 g (75%) of (E)-5-(4-bromo-2-thienyl)-4-hexenoic acid are obtained, which product is converted into 5.8 g (88%) of ethyl (E)-5-(4-bromo-2-thienyl)-4-hexenoate.

b) (E)-7-(4-Bromo-2-thienyl)-3-ethyloct-6-en-3-ol

In a manner similar to that of Example 1(d), starting with 6.3 g of ethyl (E)-5-(4-bromo-2-thienyl)-4-hexenoate (10.9 mmol), 6.6 g (100%) of the expected alcohol are obtained in the form of an orange-coloured oil.

c) [(E)-5-(4-Bromo-2-thienyl)-1,1-diethylhex-4-enyloxy] triethylsilane

In a manner similar to that of Example 1(e), starting with 6.6 g (20.3 mmol) of the above alcohol, 6.6 g (73%) of [(E)-5-(4-bromo-2-thienyl)-1,1-diethylhex-4-enyloxy] triethylsilane are obtained in the form of a colourless oil.

d) [2-((E)-5-Ethyl-1-methyl-5-triethylsilanyloxyhept-1-enyl)-4-thienyl]methanol

In a manner similar to that of Example 1(f), starting with 6.2 g (14.3 mmol) of [(E)-5-(4-bromo-2-thienyl)-1,1-diethylhex-4-enyloxy]triethylsilane, 1.7 g (29%) of [4-((E)-5-ethyl-1-methyl-5-triethylsilanyloxyhept-1-enyl)-2-thienyl]carbaldehyde are obtained, which product is reduced in the presence of NaBH$_4$ to give 1.58 g (92%) of [4-((E)-5-ethyl-1-methyl-5-triethylsilanyloxyhept-1-enyl)-2-thienyl]methanol.

e) Dimethyl 4-[2-((E)-5-Ethyl-1-methyl-5-triethylsilanyloxyhept-1-enyl)-4-thienylmethoxy]phthalate In a manner similar to that of Example 1(g), starting with 500 mg of the above alcohol, 220 mg (30%) of dimethyl 4-[2-((E)-5-ethyl-1-methyl-5-triethylsilanyloxyhept-1-enyl)-4-thienylmethoxy]phthalate are obtained in the form of a yellow oil.

f) Dimethyl 4-[2-((E)-5-Ethyl-5-hydroxy-1-methylhept-1-enyl)-4-thienylmethoxy]phthalate In a manner similar to that of Example 1(h), starting with 210 mg (0.36 mmol) of dimethyl 4-[2-((E)-5-ethyl-1-methyl-5-triethylsilanyloxyhept-1-enyl)-4-thienylmethoxy] phthalate, 90 mg (53%) of dimethyl 4-[2-((E)-5-ethyl-5-hydroxy-1-methylhept-1-enyl)-4-thienylmethoxy]phthalate are obtained.

g) (E)-7-[4-(3,4-bis-Hydroxymethyl-phenoxymethyl)-2-thienyl]-3-ethyloct-6-en-3-ol In a manner similar to that of Example 1(i), by treatment of dimethyl 4-[4-((E)-5-ethyl-5-hydroxy-1-methylhept-1-enyl)-2-thienylmethoxy]phthalate (61 mg; 0.13 mmol) with 20 mg of lithium aluminium hydride, a white solid (m.p.: 95–97° C.) is obtained after purification by chromatography on a column of silica (m=39 mg; Y=73%).

$^1$H NMR (DMSO): 0.77 (t, 6H, J=7.3 Hz), 1.36 (q, 4H, J=7.3 Hz), 1.94 (s, 3H), 2.0–2.15 (m, 2H), 3.89 (s, 1H), 4.41 (d, 2H, J=5.3 Hz), 4.50 (d, 2H, J=5.3 Hz), 4.92 (t, 1H), 5.08 (t, 1H), 5.17 (s, 2H), 5.85 (t, 1H), 6.80–6.88 (m, 2H), 7.02 (m, 2H), 7.2 (m, 2H).

EXAMPLE 3

(E)-7-[2-(3,4-bis-Hydroxymethyl-phenoxymethyl)-4-thienyl]-3-ethyloct-6-en-3-ol a) Ethyl (E)-5-(2-Bromo-4-thienyl)-4-hexenoate In a manner similar to that of Example 1(c), by reaction of 19.1 g (44.6 mmol) of (3-carboxypropyl) triphenylphosphonium bromide with 6.1 g (29.7 mmol) of 1-(2-bromo-4-thienyl)ethanone, 5.9 g (72%) of (E)-5-(2-bromo-4-thienyl)-4-hexenoic acid are obtained, which product is converted into 4.1 g (63%) of ethyl (E)-5-(2-bromo-4-thienyl)-4-hexenoate.

b) (E)-7-(2-Bromo-4-thienyl)-3-ethyloct-6-en-3-ol

In a manner similar to that of Example 1(d), starting with 4.1 g of ethyl (E)-5-(2-bromo-4-thienyl)-4-hexenoate (13.5 mmol), 3.2 g (75%) of the expected alcohol are obtained in the form of an orange-coloured oil.

c) [(E)-5-(2-Bromo-4-thienyl)-1,1-diethylhex-4-enyloxy] triethylsilane

In a manner similar to that of Example 1(e), starting with 3.2 g (11 mmol) of the above alcohol, 4.2 g (96%) of [(E)-5-(2-bromo-4-thienyl)-1,1-diethylhex-4-enyloxy] triethylsilane are obtained in the form of a colourless oil.

d) [4-((E)-5-Ethyl-1-methyl-5-triethylsilanyloxyhept-1-enyl)-2-thienyl]methanol

In a manner similar to that of Example 1(f), starting with 4.1 g (9.5 mmol) of [(E)-5-(2-bromo-4-thienyl)-1,1-diethylhex-4-enyloxy]triethylsilane, 2 g (55%) of [4-((E)-5-ethyl-1-methyl-5-triethylsilanyloxyhept-1-enyl)-2-thienyl] carbaldehyde, which product is reduced in the presence of NaBH$_4$ to give 2 g (99%) of [4-((E)-5-ethyl-1-methyl-5-triethylsilanyloxyhept-1-enyl)-2-thienyl]methanol.

e) Dimethyl 4-[4-((E)-5-Ethyl-1-methyl-5-triethylsilanyloxyhept-1-enyl)-2-thienylmethoxy]phthalate In a manner similar to that of Example 1(g), starting with 1 g (2.6 mmol) of the above alcohol, 400 mg (27%) of dimethyl 4-[4-((E)-5-ethyl-1-methyl-5-triethylsilanyloxyhept-1-enyl)-2-thienylmethoxy]phthalate are obtained in the form of a yellow oil.

f) Dimethyl 4-[4-((E)-5-Ethyl-5-hydroxy-1-methylhept-1-enyl)-2-thienylmethoxy]phthalate In a manner similar to that of Example 1(h), starting with 350 mg (0.6 mmol) of dimethyl 4-[4-((E)-5-ethyl-1-methyl-5-triethylsilanyloxyhept-1-enyl)-2-thienylmethoxy] phthalate, 190 mg (68%) of dimethyl 4-[4-((E)-5-ethyl-5-hydroxy-1-methylhept-1-enyl)-2-thienylmethoxy]phthalate are obtained.

g) (E)-7-[2-(3,4-bis-Hydroxymethyl-phenoxymethyl)-4-thienyl]-3-ethyloct-6-en-3-ol In a manner similar to that of Example 1(i), by treatment of dimethyl 4-[5-((E)-5-ethyl-5-hydroxy-1-methylhept-1-enyl)-3-thienylmethoxy]phthalate (180 mg; 0.39 mmol) with 36 mg of lithium aluminium hydride (0.9 mmol), a colourless oil is obtained after purification by chromatography on a column of silica (m=115 mg; Y=73%).

$^1$H NMR (DMSO): 0.85 (t, 6H, J=7.3 Hz), 1.43 (q, 4H, J=7.4 Hz), 1.98 (s, 3H), 2.13–2.20 (m, 2H), 3.95 (s, 1H), 4.49 (d, 2H, J=5.3 Hz), 4.58 (d, 2H, J=5.3 Hz), 5.00 (t, 1H, J=5.4 Hz), 5.16 (t, 1H, J=5.5 Hz), 5.27 (s, 2H), 5.98 (t, 1H), 6.92 (dd, 1H, J$_1$=2.6 Hz, J$_2$=8.3 Hz), 7.10 (d, 1H, J=2.5 Hz), 7.28–7.35 (m, 2H), 7.44 (s, 1H).

EXAMPLE 4

(E)-7-[6-(3,4-bis-Hydroxymethyl-phenoxymethyl)-2-pyridyl]-3-ethylnon-6-en-3-ol a) Ethyl (E)-5-(6-Bromo-2-pyridyl)-4-heptenoate In a manner similar to that of Example 1(c), by reaction of 29.8 g (69.3 mmol) of (3-carboxypropyl) triphenylphosphonium bromide with 9.9 g (46.2 mmol) of 1-(6-bromo-2-pyridyl)propanone, 8.9 g (68%) of (E)-5-(6-bromo-2-pyridyl)-4-heptenoic acid are obtained, which product is converted into 7.8 g (80%) of ethyl (E)-5-(6-bromo-2-pyridyl)-4-heptenoate.

b) (E)-7-(6-Bromo-2-pyridyl)-3-ethylnon-6-en-3-ol

In a manner similar to that of Example 1(d), starting with 7.4 g of ethyl (E)-5-(6-bromo-2-pyridyl)-4-heptenoate (23.7 mmol), 7.3 g (94%) of the expected alcohol are obtained in the form of an orange-coloured oil.

c) [(E)-5-(6-Bromo-2-pyridyl)-1,1-diethylhept-4-enyloxy]triethylsilane

In a manner similar to that of Example 1(e), starting with 7.5 g (23 mmol) of the above alcohol, 9.8 g (97%) of [(E)-5-(6-bromo-2-pyridyl)-1,1-diethylhept-4-enyloxy]triethylsilane are obtained in the form of a colourless oil.

d) [6-((E)-1,5-Diethyl-5-triethylsilanyloxyhept-1-enyl)-2-pyridyl]methanol

In a manner similar to that of Example 1(f), starting with 8.8 g (20 mmol) of [(E)-5-(6-bromo-2-pyridyl)-1,1-diethylhept-4-enyloxy]triethylsilane, 5.8 g (75%) of [6-((E)-1,5-diethyl-5-triethylsilanyloxyhept-1-enyl)-2-pyridyl]carbaldehyde, which product is reduced in the presence of NaBH$_4$ to give 5.8 g (99%) of [6-((E)-1,5-diethyl-5-triethylsilanyloxyhept-1-enyl)-2-pyridyl]methanol.

e) Dimethyl 4-[6-((E)-1,5-Diethyl-5-triethylsilanyloxyhept-1-enyl)-2-pyridylmethoxy]phthalate In a manner similar to that of Example 1(g), starting with 1 g (2.55 mmol) of the above alcohol, 1.2 g (81%) of dimethyl 4-[6-((E)-1,5-diethyl-5-triethylsilanyloxyhept-1-enyl)-2-pyridylmethoxy]phthalate are obtained in the form of a yellow oil.

f) Dimethyl 4-[6-((E)-1,5-Diethyl-5-hydroxyhept-1-enyl)-2-pyridylmethoxy]phthalate In a manner similar to that of Example 1(h), starting with 1.1 g (1.88 mmol) of dimethyl 4-[6-((E)-1,5-diethyl-5-triethylsilanyloxyhept-1-enyl)-2-pyridylmethoxy]phthalate, 740 mg (84%) of dimethyl 4-(6-((E)-1,5-diethyl-5-hydroxyhept-1-enyl)-2-pyridylmethoxy]phthalate are obtained.

g) (E)-7-[6-(3,4-bis-Hydroxymethyl-phenoxymethyl)-2-pyridyl]-3-ethylnon-6-en-3-ol]-3-ethyloct-6-en-3-ol In a manner similar to that of Example 1(i), by treatment of dimethyl 4-[6-((E)-1,5-diethyl-5-hydroxyhept-1-enyl)-2-pyridylmethoxy]phthalate (740 mg; 1.57 mmol) with 145 mg of lithium aluminium hydride (3.8 mmol), a colourless oil is obtained after purification by chromatography on a column of silica (m=515 mg; Y=79%).

$^1$H NMR (CDCl$_3$): 0.88 (t, 6H, J=7.4 Hz), 1.04 (t, 3H, J=7.5 Hz), 1.48–1.64 (m, 6H), 1.7 (bs, 1H), 2.24–2.33 (m, 2H), 2.65 (q, 2H, J=7.5 Hz), 3.1 (bs, 1H), 3.3 (bs, 1H), 4.65 (s, 2H), 4.68 (s, 2H), 5.16 (s, 2H), 6.24 (t, 1H, J=7.3 Hz), 6.88 (dd, 1H, J$_1$=2.6 Hz, J$_2$=8.3 Hz), 7.03 (d, 1H, J=2.6 Hz), 7.20–7.32 (m, 3H), 7.62 (t, 1H, J=7.8 Hz).

EXAMPLE 5

(E)-7-[5-(3,4-bis-Hydroxymethyl-phen(oxymethyl)-3-pyridyl]-3-ethylnon-6-en-3-ol a) 5-Bromo-N-methoxy-N-methylnicotinamide 40 g (198 mmol) of 5-bromonicotinic acid are dissolved in 300 mL of THF and treated with 19 mL of oxalyl chloride at 0° C. 66 mL (475 mmol) of triethylamine are then added, followed by 23.2 g (237 mmol) of N,O-dimethylhydroxylamine hydrochloride. After stirring at room temperature for 4 hours, the reaction medium is poured into water and extracted with ethyl acetate. The organic phase is separated out after settling, dried over magnesium sulphate and evaporated. 45.1 g (93%) of the expected product are collected in the form of a light brown oil.

b) 1-(5-Bromo-3-pyridyl)propanone 44 g (180 mmol) of 5-bromo-N-methoxy-N-methylnicotinamide are dissolved in 200 mL of THF and 60 mL (180 mmol) of ethylmagnesium chloride solution (3M in ethyl ether) are added dropwise. The reaction medium is stirred at room temperature for one hour, poured into water and extracted with ethyl acetate. The organic phase is separated out after settling, dried over magnesium sulphate and evaporated. The residue obtained is purified by chromatography on a column of silica eluted with a mixture of heptane and ethyl acetate (70/30). 4 g (11%) of 1-(5-bromo-3-pyridyl)propanone are collected.

c) Ethyl (E)-5-(5-Bromo-3-pyridyl)-4-heptenoate

In a manner similar to that of Example 1(c), by reaction of 12 g (28 mmol) of (3-carboxypropyl)triphenylphosphonium bromide with 4 g (18.6 mmol) of 1-(5-bromo-3-pyridyl)propanone, 4.45 g (84%) of (E)-5-(5-bromo-3-pyridyl)-4-heptenoic acid are obtained, which product is converted into 3.6 g (74%) of ethyl (E)-5-(5-bromo-3-pyridyl)-4-heptenoate.

d) (E)-7-(5-Bromo-3-pyridyl)-3-ethylnon-6-en-3-ol

In a manner similar to that of Example 1(d), starting with 2.6 g of ethyl (E)-5-(5-bromo-3-pyridyl)-4-heptenoate (8.3 mmol), 2.3 g (85%) of the expected alcohol are obtained in the form of an orange-coloured oil.

e) [(E)-5-(5-Bromo-3-pyridyl)-1,1-diethylhept-4-enyloxy]triethylsilane

In a manner similar to that of Example 1(e), starting with 2.3 g (7 mmol) of the above alcohol, 2.9 g (93%) of [(E)-5-(5-bromo-3-pyridyl)-1,1-diethylhept-4-enyloxy]triethylsilane are obtained in the form of a colourless oil.

f) [5-((E)-1,5-Diethyl-5-triethylsilanyloxyhept-1-enyl)-3-pyridyl]methanol

In a manner similar to that of Example 1(f), starting with 2.9 g (6.6 mmol) of [(E)-5-(5-bromo-3-pyridyl)-1,1-diethylhept-4-enyloxy]triethylsilane, 775 mg (30%) of [5-((E)-1,5-diethyl-5-triethylsilanyloxyhept-1-enyl)-3-pyridyl]carbaldehyde are obtained, which product is reduced in the presence of NaBH$_4$ to give 774 mg (99%) of [5-((E)-1,5-diethyl-5-triethylsilanyloxyhept-1-enyl)-3-pyridyl]methanol.

g) Dimethyl 4-[5-((E)-1,5-Diethyl-5-triethylsilanyloxyhept-1-enyl)-3-pyridylmethoxy]phthalate In a manner similar to that of Example 1(g), starting with 750 mg (1.9 mmol) of the above alcohol, 140 mg (13%) of dimethyl 4-[5-((E)-1,5-diethyl-5-triethylsilanyloxyhept-1-enyl)-3-pyridylmethoxy]phthalate are obtained in the form of a yellow oil.

h) Dimethyl 4-[5-((E)-1,5-Diethyl-5-hydroxyhept-1-enyl)-3-pyridylmethoxy]phthalate In a manner similar to that of Example 1(h), starting with 100 mg (0.17 mmol) of dimethyl 4-[5-((E)-1,5-diethyl-5-triethylsilanyloxyhept-1-enyl)-3-pyridylmethoxy]phthalate, 66 mg (82%) of dimethyl 4-[5-((E)-1,5-diethyl-5-hydroxyhept-1-enyl)-3-pyridylmethoxy]phthalate are obtained.

i) (E)-7-[5-(3,4-bis-Hydroxymethyl-phenoxymethyl)-3-pyridyl]-3-ethylnon-6-en-3-ol In a manner similar to that of Example 1(i), by treatment of 60 mg (0.13 mmol) of dimethyl 4-[5-((E)-1,5-diethyl-5- hydroxyhept-1-enyl)-3-pyridylmethoxy]phthalate with 12 mg of lithium aluminium hydride, a colourless oil is obtained after purification by chromatography on a column of silica (m=25 mg; Y=47%).

$^1$H NMR (CDCl$_3$): 0.90 (t, 6H, J=7.4 Hz), 0.98 (t, 3H, J=7.4 Hz), 1.48–1.60 (m, 6H), 2.20–2.26 (m, 2H), 2.52 (q, 2H, J=7.4 Hz), 4.69 (s, 2H), 4.71 (s, 2H), 5.04 (s, 2H), 5.69 (t, 1H, J=7.3 Hz), 6.87 (dd, 1H, J$_1$=2.7 Hz, J$_2$=8.3 Hz), 7.02, (d, 1H, J=2.6 Hz), 7.25–7.28 (m, 1H), 7.72 (m, 2H), 8.4 (bs, 1H), 8.5 (bs, 1H).

EXAMPLE 6

(E)-7-[5-(3,4-bis-Hydroxymethyl-phenoxymethyl)-2-thienyl]-3-ethylnon-6-en-3-ol a) 2-Ethyl-2–2-thienyl-[1,3]dioxolane 30 g (214.3 mmol) of 1-2-thienyl-1-propanone are dissolved in 120 mL of ethylene glycol. 93 g (856 mmol) of trimethylsilyl chloride are then added. The reaction medium is stirred at room temperature for 24 hours. After treatment with water, the medium is extracted with ethyl acetate and the organic phases are then combined, dried and concentrated under reduced pressure. The residue obtained is purified by chromatography on a column of silica (eluent: 90 heptane/10 ethyl acetate). A yellow oil is obtained (m=15 g; Y=38%).

b) 5-(2-Ethyl-[1,3]dioxolan-2-yl)thiophene-2-carbaldehyde 15 g (81.4 mmol) of 2-ethyl-2-2-thienyl-[1,3]dioxolane are dissolved in 300 mL of anhydrous THF and the mixture is then cooled to –78° C. 53 mL (89 mmol) of 1.7 M tert-butyllithium solution are then added, after which the reaction medium is stirred for 1 hour. 10 mL (120 mmol) of anhydrous DMF are then added and the medium is stirred for 1 hour. The reaction medium is treated at –78° C. with 1N hydrochloric acid solution and is then extracted with ethyl acetate and the organic phases are combined, dried and concentrated under reduced pressure. The residue obtained is purified by chromatography on a column of silica. A yellow oil is obtained (m=19 g; Y=100%).

c) [5-(2-Ethyl-[1,3]dioxolan-2-yl)-2-thienyl]methanol 9.5 g (44.7 mmol) of 5-(2-ethyl-[1,3]dioxolan-2-yl) thiophene-2-carbaldehyde are dissolved in 100 mL of anhydrous methanol and the mixture is then cooled to 0° C.

2.2 g (58.1 mmol) of sodium borohydride are then added portionwise. After stirring for 1 hour, the medium is treated with ammonium chloride solution and extracted with ethyl acetate. The organic phases are combined, dried and concentrated under reduced pressure. After purification by chromatography on a column of silica, a yellow oil is obtained (m=9.25 g; Y=96%).

d) 5-(2-Ethyl-[1,3]dioxolan-2-yl)-2-thienylmethyl Methanesulphonate 9.25 g (43.2 mmol) of [5-(2-ethyl-[1,3]dioxolan-2-yl)-2-thienyl]methanol are dissolved in 500 mL of dichloromethane and cooled to 0° C. 9.0 mL (64.7 mmol) of triethylamine are added, followed by 3.5 mL of methylsulphonyl chloride (45.3 mmol). After stirring for 1 hour, the reaction medium is treated with ammonium chloride solution and extracted with dichloromethane. The organic phases are combined, dried and concentrated under reduced pressure. A brown oil is obtained (m=9.28 g; Y=75%).

e) Dimethyl 4-[5-(2-Ethyl-[1,3]dioxolan-2-yl)-2-thienylmethoxy]phthalate 9.25 g (43.2 mmol) of 5-(2-ethyl-[1,3]dioxolan-2-yl)-2-thienylmethyl methanesulphonate are dissolved in 100 mL of 2-butanone, and 9.07 g (43.2 mmol) of dimethyl 4-hydroxyphthalate (prepared in Example 1(b)), 6 g of potassium carbonate (43.2 mmol) and 20 mg of sodium iodide are added. The mixture is refluxed for 12 hours, cooled and filtered. The filtrate is concentrated under reduced pressure and then purified by chromatography on a column of silica. A yellow oil is obtained (m=12.70 g; Y=73%).

f) {5-[5-(2-Ethyl-[1,3]dioxolan-2-yl)-2-thienylmethoxy]-2-hydroxymethylphenyl}methanol 12.7 g (31.5 mmol) of dimethyl 4-[5-(2-ethyl-[1,3] dioxolan-2-yl)-2-thienylmethoxy]phthalate are dissolved in 500 mL of anhydrous ethyl ether. 2.87 g (75.7 mmol) of lithium aluminium hydride are added and the reaction medium is stirred at 0° C. for 1 hour. 2.9 mL of water are then added slowly, followed by 2.9 mL of aqueous 15% sodium hydroxide, and then 8.7 mL of water are also added slowly. After stirring for 20 minutes, the medium is then filtered. The filtrate is concentrated under reduced pressure and the residue obtained is then purified by chromatography on a column of silica. A white solid (m.p.: 78–80° C.) is obtained (m=8 g; Y=72%).

g) 1-[5-(3,4-bis-Hydroxymethyl-phenoxymethyl)-2-thienyl]-1-propanone 8 g (22.8 mmol) of {5-[5-(2-ethyl-[1,3]dioxolan-2-yl)-2-thienylmethoxy]-2-hydroxymethylphenyl}methanol are dissolved in 75 mL of water and 75 mL of acetone. 1 g of para-toluenesulphonic acid is then added and the reaction medium is refluxed for 1 hour. The reaction medium is treated with sodium bicarbonate solution and extracted with ethyl acetate. The organic phases are combined, washed with water, dried and concentrated under reduced pressure. A white powder (m.p.=123° C.) is obtained (m=6.9 g; Y=100%).

h) 1-{5-[3,4-bis(tert-Butyldimethylsilanyloxymethyl) phenoxymethyl]-2-thienyl}-1-propanone 6.9 g (22.8 mmol) of 1-[5-(3,4-bis-hydroxymethyl-phenoxymethyl)-2-thienyl]-1-propanone are dissolved in 70 mL of anhydrous DMF. 4.3 g (63.8 mmol) of imidazole and 7.5 g (50 mmol) of tert-butyldimethylchlorosilane are then added portionwise. The reaction medium is stirred at room temperature for 12 hours. The resulting mixture is treated with water and extracted with ethyl acetate. The organic phases are combined, dried and concentrated under reduced pressure and the residue obtained is then purified by chromatography on a column of silica. A colourless oil is obtained (m=11.5 g; Y=100%).

i) (E)-5-{5-[3,4-bis(tert-Butyldimethylsilanyloxymethyl) phenoxymethyl]-2-thienyl}-4-heptenoic Acid 6.7 g (15.6 mmol) of (3-carboxypropyl) triphenylphosphonium bromide are dried under vacuum for 1 h by heating at 130° C. and then cooled to room temperature and dissolved in 70 mL of anhydrous THF. 3.5 g (31.2 mmol) of potassium tert-butoxide are then added slowly and the orange-red mixture is then stirred for 15 minutes. A solution of 5.7 g (10.4 mmol) of 1-{5-[3,4-bis(tert-butyldimethylsilanyloxymethyl)phenoxymethyl]-2-thienyl}-1-propanone in 70 mL of THF is then added dropwise and the reaction medium is stirred for 4 hours. After treatment with saturated ammonium chloride solution, extraction with ethyl acetate, drying and evaporation of the solvents from the organic phase, the residue obtained is purified by chromatography on a column of silica. A yellow oil is obtained (m=4.3 g; Y=66%).

j) Methyl (E)-5-{5-[3,4-bis(tert-Butyldimethylsilanyloxymethyl)phenoxymethyl)-2-thienyl}-4-heptenoate 4.3 g (7.1 mmol) of (E)-5-{5-[3,4-bis(tert-butyldimethylsilanyloxymethyl)phenoxymethyl]-2-thienyl}-4-heptenoic acid are dissolved in 70 mL of 2-butanone, and 1.1 g of potassium carbonate (7.8 mmol) and 2.2 mL of iodomethane (35 mmol) are added. The medium is refluxed for 12 hours, cooled and filtered. The filtrate is concentrated under reduced pressure and then purified by chromatography on a column of silica. A yellow oil is obtained (m=4.34 g; Y=98%).

k) (E)-7-{5-[3,4-bis(tert-Butyldimethylsilanyloxymethyl) phenoxymethyl]-2-thienyl}-3-ethylnon-6-en-3-ol 1.3 g (2.3 mmol) of methyl (E)-5-{5-[3,4-bis(tert-butyldimethylsilanyloxymethyl)phenoxymethyl]-2-thienyl}-4-heptenoate are dissolved in 20 mL of ethyl ether. 2.2 mL of 3.0 M ethylmagnesium bromide solution (6.5 mmol) are then added dropwise and the reaction medium is stirred at room temperature for 2 hours. After treatment with saturated ammonium chloride solution, extraction with ethyl acetate and then drying and evaporation of the solvents from the organic phase, the residue obtained is purified by chromatography on a column of silica. After separation of the Z isomer from the E isomer, a colourless oil is obtained (m=440 mg; y=29%).

l) (E)-7-[5-(3,4-bis-Hydroxymethyl-phenoxymethyl)-2-thienyl]-3-ethylnon-6-en-3-ol 440 mg (0.7 mmol) of (E)-7-{4-[3,4-bis(tert-butyldimethylsilanyloxymethyl)phenoxymethyl] cyclopenta-1,3-dienyl}-3-ethylnon-6-en-3-ol are dissolved in 20 mL of THF. 2.0 mL (2.0 mmol) of 1.0 M tetrabutylammonium fluoride solution are added and the reaction medium is stirred at room temperature for 1 hour. After treatment with ammonium chloride solution and extraction with ethyl acetate, the organic phases are combined, dried and concentrated under reduced pressure. The residue is purified by chromatography on a column of silica (eluent: 80 ethyl acetate/20 heptane). A white powder (m.p.: 82° C.) is obtained (m=248 mg; Y=89%).

$^1$H NMR (DMSO): 0.82 (t, 6H, J=7.5 Hz); 1.07 (t, 3H, J=7.4 Hz); 1.36–1.46 (m, 6H); 2.03 (s, 1H); 2.10–2.20 (m, 2H); 2.42–2.51 (m, 2H); 4.47 (d, 2H, J=4.9 Hz); 4.56 (d, 2H, J=4.9 Hz); 4.99 (t, 1H, J=4.9 Hz); 5.15 (t, 1H, J=4.9 Hz); 5.23 (s, 2H); 5.82 (t, 1H, J=7.3 Hz); 6.87–6.96 (m, 2H); 7.08 (d, 2H, J=2.8 Hz); 7.28 (d, 1H, 8.3 Hz).

EXAMPLE 7

(4E,6E)-7-[5-(3,4-bis-Hydroxymethyl-phenoxymethyl)-2-thienyl]-3-ethylnona-4,6-dien-3-ol a) Ethyl (E)-3-{5-[3,4-bis(tert-Butyldimethylsilanyloxymethyl)phenoxymethyl]-2-thienyl)-2-pentenoate 4.1 mL (20 mmol) of triethyl phosphonoacetate are dissolved in 100 mL of anhydrous THF and NaH (0.8 g, 20 mmol) is then added portionwise. After stirring for 30 minutes, a solution of 5.75 g (10.4 mmol) of 1-{5-[3,4-bis(tert-butyldimethylsilanyloxymethyl)phenoxymethyl]-2-thienyl}-1-propanone (prepared in Example 6(h)) in 50 mL of anhydrous THF is added dropwise and the reaction medium is heated for 14 hours at 50° C. After the usual treatment and chromatography on silica gel (eluent: 90 heptane/10 ethyl acetate), the desired product is separated from its Z isomer and obtained in the form of a colourless oil (m=3.18 g; Y=50%).

b) (E)-3-{5-[3,4-bis(tert-Butyldimethyl-silanyloxymethyl) phenoxymethyl]-2-thienyl}pent-2-en-1-ol 3.18 g (5.2 mmol) of ethyl (E)-3-{5-[3,4-bis(tert-butyldimethylsilanyloxymethyl)phenoxymethyl]-2-thienyl}-2-pentenoate dissolved in 20 mL of ethyl ether are added dropwise to a suspension of lithium aluminium hydride (0.24 g, 6.3 mmol) in 50 mL of ether. The medium is stirred at room temperature for 2 hours and then treated successively with 240 μL of water, 240 μL of 15% sodium hydroxide and 720 μL of water. The medium is then filtered and the filtrate is concentrated under reduced pressure. The desired product (m=2.92 g; Y=93%) is obtained in the form of a colourless oil.

c) (E)-3-{5-[3,4-bis(tert-Butyldimethylsilanyloxy-methyl) phenoxymethyl]-2-thienyl}pent-2-enal 2.74 g (5.1 mmol) of (E)-3-{5-[3,4-bis(tert-butyldimethylsilanyloxymethyl)phenoxymethyl]-2-thienyl}pent-2-en-1-ol are dissolved in 80 mL of dichloromethane and placed under a nitrogen atmosphere. 4.45 g (51 mmol) of manganese dioxide are added and the medium is stirred for 14 hours. After filtration and then evaporation, a yellow oil is obtained. The crude product (2.9 g) is the expected aldehyde, obtained in a quantitative yield.

d) Ethyl (2E,4E)-5-{5-[3,4-bis(tert-Butyldimethyl-silanyloxymethyl)phenoxymethyl]-2-thienyl}hepta-2,4-dienoate In a manner similar to that of Example 7(a), by reaction of 2.9 g (5.1 mmol) of (E)-3-{5-[3,4-bis(tert-butyldimethylsilanyloxymethyl)phenoxymethyl]-2-thienyl}pent-2-enal with 1.5 mL (7.6 mmol) of triethyl phosphonoacetate, a single isomer is obtained. Ethyl (2E,4E)-5-{5-[3,4-bis(tert-butyldimethyl-silanyloxymethyl) phenoxymethyl]-2-thienyl}hepta-2,4-dienoate is isolated in the form of a yellow oil (m=2.17 g; Y=67%).

e) (4E,6E)-7-{5-[3,4-bis(tert-Butyldimethyl-silanyloxymethyl)phenoxymethyl]-2-thienyl}-3-ethylnona-4,6-dien-3-ol An ethyllithium solution (1.5 M) is prepared by slow addition of a solution of ethyl bromide (11.2 mL, 150 mmol) in 50 mL of pentane to a suspension of lithium (2.75 g, 400 mmol) in 50 mL of pentane at 40° C., followed by stirring at 40° C. for 12 hours. After cooling to room temperature, 23 mL (34 mmol) of this solution are added dropwise to a solution at 0° C. of ethyl (2E,4E)-5-{5-[3,4-bis(tert-butyldimethylsilanyl-oxymethyl)phenoxymethyl]-2-thienyl}hepta-2,4-dienoate in 50 mL of THF. The medium turns red and is stirred for 2 hours at 0° C. and then treated by addition of saturated ammonium chloride solution. After the usual treatment, the residue is purified by chromatography on silica gel (eluent: 95 heptane/5 ethyl acetate). The desired product is obtained in the form of a yellow oil (m=0.85 g, Y=38%).

f) (4E,6E)-7-[5-(3,4-bis-Hydroxymethyl-phenoxymethyl)-2-thienyl]-3-ethylnona-4,6-dien-3-ol 850 mg (1.3 mmol) of (4E,6E)-7-{5-[3,4-bis(tert-butyldimethylsilanyloxymethyl)phenoxymethyl]-2-thienyl}-3-ethylnona-4,6-dien-3-ol are dissolved in 20 mL of anhydrous THF. 3.9 mL (3.9 mmol) of 1 M tetrabutylammonium fluoride solution are then added and the medium is stirred for 4 hours. After the usual treatment, the residue is purified by chromatography on silica gel (eluent: 2 heptane/8 ethyl acetate). (4E,6E)-7-[5-(3,4-bis-Hydroxymethyl-phenoxymethyl)-2-thienyl]-3-ethylnona-4,6-dien-3-ol is obtained in the form of a yellow oil (m=340 mg; Y=63%).

$^1$H NMR (DMSO): 0.74 (t, 6H, J=7.5 Hz); 1.13 (t, 3H, J=7.4 Hz); 1.36–1.45 (m, 4H); 2.26 (t, 1H, J=6.9 Hz); 2.46–2.53 (m, 2H); 4.38 (d, 2H, J=4.8 Hz); 4.47 (d, 2H, J=4.8 Hz); 4.90 (t, 1H, J=4.8 Hz); 5.05 (t, 1H, J=4.8 Hz); 5.16 (s, 2H); 5.76 (d, 1H, J=13.8 Hz); 6.36–6.47 (m, 2H); 6.79–6.83 (m, 1H); 6.98–7.04 (m, 3H); 7.20 (d, 1H, J=8.3 Hz).

EXAMPLE 8

(E)-7-{5-[2-(3,4-bis-Hydroxymethyl-phenyl)ethyl]-2-thienyl}-3-ethylnon-6-en-3-ol a) Dimethyl 4-{(E)-2-[5-(2-Ethyl-[1,3]dioxolan-2-yl)-2-thienyl]vinyl}phthalate 18.5 g (53.7 mmol) of dimethyl 4-(diethoxyphosphorylmethyl)phthalate and 9.5 g (44.7 mmol) of 5-(2-ethyl-[1,3]dioxolan-2-yl)thiophene-2-carbaldehyde (described in Example 6(b)) are dissolved in 200 mL of anhydrous THF. 6.02 g (53.7 mmol) of potassium tert-butoxide are added and the mixture is stirred for 24 h. After the usual treatment and chromatography on silica gel (eluent: 8 heptane/2 ethyl acetate), the desired product is obtained in the form of a yellow oil (m=9.53 g, Y=53%).

b) Dimethyl 4-{2-[5-(2-Ethyl-[1,3]dioxolan-2-yl)-2-thienyl]ethyl}phthalate 9.3 g (23 mmol) of dimethyl 4-{(E)-2-[5-(2-ethyl-[1,3]dioxolan-2-yl)-2-thienyl]vinyl}phthalate are dissolved in 150 mL of dioxane and 1 mL of triethylamine is then added. The mixture is degassed using a stream of nitrogen and 9.3 g of 5% palladium-on-charcoal are then added to the reaction medium. A positive pressure of hydrogen is maintained in the reaction medium for 5 hours, with heating at 80° C. After cooling and then filtration through Celite and evaporation, the desired product is obtained in the form of a yellow oil (m=9.4 g; Y=100%).

c) 4-{2-[5-(2-Ethyl-[1,3]dioxolan-2-yl)-2-thienyl]ethyl}-2-hydroxymethylphenyl)methanol In a manner similar to that of Example 6(f), by reaction of 9.3 g (23 mmol) of dimethyl 4-{2-[5-(2-ethyl-[1,3]dioxolan-2-yl)-2-thienyl]ethyl}phthalate with 2.2 g (58 mmol) of lithium aluminium hydride, the desired product is obtained in the form of a colourless oil (m=8.7 g; Y=100%).

d) 1-{5-[2-(3,4-bis-Hydroxymethyl-phenyl)ethyl]-2-thienyl}-1-propanone

In a manner similar to that of Example 6(g), by reaction of 8.7 g (23 mmol) of (4-{2-[5-(2-ethyl-[1,3]dioxolan-2-yl)-2-thienyl]ethyl}-2-hydroxymethylphenyl)methanol with a solution of para-toluenesulphonic acid in an acetone/water mixture, the desired product is obtained in the form of a white powder (m=5.41 g; Y=71%).

e) 1-{5-[2-(3,4-bis(tert-Butyldimethylsilanyloxy-methyl)phenyl)ethyl]-2-thienyl}-1-propanone In a manner similar to that of Example 6(h), by reaction of 5.4 g (17.7 mmol) of 1-{5-[2-(3,4-bis-hydroxymethyl-phenyl)ethyl]-2-thienyl}-1-propanone with 3.37 g (49 mmol) of imidazole and 5.86 g (39 mmol) of tert-butyldimethylchlorosilane, the desired product is obtained in the form of a colourless oil (m=9.4 g; Y=100%).

f) (E)-5-{5-[2-(3,4-bis(tert-Butyldimethylsilanyloxy-methyl)phenyl)ethyl]-2-thienyl}-4-heptenoic Acid In a manner similar to that of Example 6(i), by reaction of 5.08 g (9.5 mmol) of 1-{5-[2-(3,4-bis(tert-butyldimethylsilanyloxymethyl)phenyl)ethyl]-2-thienyl}-1-propanone with 6.1 g (14 mmol) of (3-carboxypropyl)triphenylphosphonium bromide and 3.1 g (28 mmol) of potassium tert-butoxide, the desired product is obtained in the form of a yellow oil (m=2.7 g; Y=48%).

g) Methyl (E)-5-{5-[2-(3,4-bis(tert-Butyldimethylsilanyloxymethyl)phenyl)ethyl]-2-thienyl}-4-heptenoate In a manner similar to that of Example 6(j), by reaction of 2.7 g (4.5 mmol) of (E)-5-15-[2-(3,4-bis(tert-butyldimethylsilanyloxymethyl)phenyl)ethyl]-2-thienyl}-4-heptenoic acid with 680 mg (4.9 mmol) of potassium carbonate and 1.38 mL (22.6 mmol) of methyl iodide, the desired product is obtained in the form of a yellow oil (m=1.79 g; Y=64%).

h) (E)-7-{5-[2-(3,4-bis(tert-Butyldimethylsilanyloxy-methyl)phenyl)ethyl]-2-thienyl}-3-ethylnon-6-en-3-ol In a manner similar to that of Example 6(k), by reaction of 1.79 g (2.9 mmol) of methyl (E)-5-{5-[2-(3,4-bis(tert-butyldimethylsilanyloxymethyl)phenyl)-ethyl]-2-thienyl}-4-heptenoate with 2.9 mL (8.7 mmol) of 3.0 M ethylmagnesium bromide, the desired product is obtained in the form of a colourless oil (m=710 mg; Y=38%).

i) (E)-7-{5-[2-(3,4-bis-Hydroxymethyl-phenyl)ethyl]-2-thienyl}-3-ethylnon-6-en-3-ol In a manner similar to that of Example 6(l), by reaction of 710 mg (1.1 mmol) of (E)-7-{5-[2-(3,4-bis(tert-butyldimethylsilanyloxymethyl)phenyl)ethyl]-2-thienyl}-3-ethylnon-6-en-3-ol with 3.3 mL (3.3 mmol) of 1.0 M tetrabutylammonium fluoride solution, the desired product is obtained in the form of a white powder (m.p.=77° C.; m=380 mg; Y=83%).

$^1$H NMR (DMSO): 0.74 (t, 6H, J=7.5 Hz); 0.97 (t, 3H, J=7.4 Hz); 1.26–1.35 (m, 6H); 1.99–2.09 (m, 2H); 2.34 (q, 2H, J=7.4 Hz); 2.80–2.86 (m, 2H); 2.92–2.98 (m, 2H); 3.86 (s, 1H); 4.43–4.47 (m, 4H); 4.95 (t, 1H, J=4.7 Hz); 5.00 (t, 1H, J=4.7 Hz); 5.63 (t, 1H, J=7.3 Hz); 6.65 (d, 1H, J=3.4 Hz); 6.75 (d, 1H, J=3.4 Hz); 7.04 (d, 1H, J=7.65 Hz); 7.20–7.22 (m, 2H).

EXAMPLE 9

(E)-7-[4-(3,4-bis-Hydroxymethyl-phenoxymethyl)-2-thienyl]-3-ethylnon-6-en-3-ol a) 1-(4-Bromo-2-thienyl)-1-propanol 30 g (157 mmol) of 4-bromo-2-thiophenecarboxaldehyde are dissolved in 200 mL of anhydrous THF. 104 mL (312 mmol) of 3.0 M ethylmagnesium bromide are added slowly and the medium is stirred for 2 hours at room temperature. After the usual treatment, an orange-coloured oil is obtained (m=33.5 g; Y=96%).

b) 1-(4-Bromo-2-thienyl)-1-propanone 33.5 g (151 mmol) of 1-(4-bromo-2-thienyl)-1-propanol are dissolved in 400 mL of dichloromethane. 130 g (1.5 mol) of manganese dioxide are then added portionwise and the medium is stirred at room temperature for 24 hours. After filtration through Celite and then concentration and chromatography on silica gel (eluent: 9 heptane/1 ethyl acetate), the desired product is obtained in the form of white crystals (m=26.6 g; Y=80%).

c) (E)-5-(4-Bromo-2-thienyl)-4-heptenoic Acid

In a manner similar to that of Example 6(i), by reaction of 16 g (73 mmol) of 1-(4-bromo-2-thienyl)-1-propanone with 47 g (109 mmol) of (3-carboxypropyl)triphenylphosphonium bromide and 24.6 g (219 mmol) of potassium tert-butoxide, the desired product is obtained in the form of an orange-coloured solid (m=16.7 g; Y=80%).

d) Ethyl (E)-5-(4-Bromo-2-thienyl)-4-heptenoate 16.6 g (57 mmol) of (E)-5-(4-bromo-2-thienyl)-4-heptenoic acid are dissolved in 150 mL of absolute ethanol and 1 mL of concentrated sulphuric acid is added. The mixture is refluxed for 2 hours and then cooled. After the usual treatment and chromatography on silica gel, the desired product is obtained in the form of a yellow oil (m=14.1 g; Y=77%).

e) (E)-7-(4-Bromo-2-thienyl)-3-ethylnon-6-en-3-ol

In a manner similar to that of Example 6(k), by reaction of 14.1 g (44.4 mmol) of ethyl (E)-5-(4-bromo-2-thienyl)-4-heptenoate with 60 mL (180 mmol) of 3.0 M ethylmagnesium bromide, the desired product is obtained in the form of a yellow oil (m=12.8 mg; Y=87%).

f) [(E)-5-(4-Bromo-2-thienyl)-1,1-diethylhept-4-enyloxy]triethylsilane 11.8 g (35.6 mmol) of (E)-7-(4-bromo-2-thienyl)-3-ethylnon-6-en-3-ol are dissolved in 150 mL of dichloromethane. 130 mg (1.1 mmol) of dimethylaminopyridine and 14.9 mL (107 mmol) of triethylamine are added. The reaction medium is cooled to 0° C. and 12.1 mL (53.4 mmol) of triethylsilyl trifluoromethanesulphonate are added dropwise. The medium is warmed to room temperature and stirred for 15 minutes, after which it is poured into 150 mL of water and extracted with dichloromethane. After chromatography on silica gel (eluent: heptane), the desired product is obtained in the form of a colourless oil (m=15 g; Y=100%).

g) 5-((E)-1,5-Diethyl-5-triethylsilanyloxyhept-1-enyl)thiophene-3-carbaldehyde 11 g (24.7 mmol) of [(E)-5-(4-bromo-2-thienyl)-1,1-diethylhept-4-enyloxy]triethylsilane are dissolved in 100 mL of anhydrous THF and the mixture is cooled to −78° C. 10.9 mL (27 mmol) of 2.5 M butyllithium are added slowly and the mixture is stirred for 15 minutes. 2.1 mL (27 mmol) of dimethylformamide are then added and the medium is stirred for 30 minutes and then poured into aqueous ammonium chloride solution. After extraction with ethyl acetate and chromatography on silica gel (eluent: 9 heptane/1 ethyl acetate), the product is obtained in the form of a colourless oil (m=4 g; Y=41%).

h) [5-((E)-1,5-Diethyl-5-triethylsilanyloxyhept-1-enyl)-3-thienyl]methanol 4 g (9.9 mmol) of 5-((E)-1,5-diethyl-5-triethylsilanyloxyhept-1-enyl)thiophene-3-carbaldehyde are dissolved in 50 mL of THF and 50 mL of methanol. 1 g (26 mmol) of sodium borohydride is then added portionwise. The reaction medium is stirred for 1 hour and then poured into 100 mL of water. After purification by chromatography on silica gel, the desired product is obtained in the form of a colourless oil (m=4 g; Y=100%).

i) Dimethyl 4-[5-((E)-1,5-Diethyl-5-triethylsilanyloxyhept-1-enyl)-3-thienylmethoxy]phthalate 3.9 g (9.8 mmol) of [5-((E)-1,5-diethyl-5-triethylsilanyloxyhept-1-enyl)-3-thienyl]methanol are dissolved in 100 mL of dichloromethane and the mixture is cooled to 0° C. 2 mL (15 mmol) of triethylamine are added, followed by 840 µL (10.7 mmol) of methanesulphonyl chloride. After stirring for 30 minutes, the medium is treated with ammonium chloride solution. The crude residue obtained is then dissolved in 100 mL of 2-butanone. 100 mg (0.7 mmol) of sodium iodide, 1.6 g (11.6 mmol) of potassium carbonate and 2 g (10 mmol) of dimethyl 4-hydroxyphthalate are added to this solution. The reaction medium is refluxed for 15 hours and then cooled and filtered through Celite. The residue obtained is purified by chromatography on a column of silica (eluent: 93 heptane/7 ethyl acetate). The desired product is obtained in the form of a colourless oil (m=1.7 g; Y=30%).

j) Dimethyl 4-[5-((E)-1,5-Diethyl-5-hydroxyhept-1-enyl)-3-thienylmethoxy]phthalate 1.7 g (2.9 mmol) of dimethyl 4-[5-((E)-1,5-diethyl-5-triethylsilanyloxyhept-1-enyl)-3-thienylmethoxy]phthalate are dissolved in 50 mL of anhydrous THF. 3.5 mL (3.5 mmol) of tetrabutylammonium fluoride (1.0 M in THF) are added and the medium is stirred at 60° C. for 3 hours. After the usual treatment and purification on silica gel (eluent: 70 heptane/30 ethyl acetate), the desired product is obtained in the form of a yellow oil (m=710 mg; Y=51%).

k) (E)-7-[4-(3,4-bis-Hydroxymethyl-phenoxymethyl)2-thienyl]-3-ethylnon-6-en-3-ol 480 mg (1.1 mmol) of dimethyl 4-[5-((E)-1,5-diethyl-5-hydroxyhept-1-enyl)-3-thienylmethoxy]phthalate are dissolved in 10 mL of ethyl ether. This solution is added to a suspension of 130 mg (3.4 mmol) of lithium aluminium hydride and the reaction medium is stirred for 15 minutes. The reaction medium is then treated by successive addition of 130 µL of water, 130 µL of 15% sodium hydroxide and 400 µL of water. After filtration and chromatography on silica gel (eluent: 2 heptane/8 ethyl acetate), the desired product is obtained in the form of white crystals (m.p.= 63–64° C.; m=380 mg; Y=90%).

$^1$H NMR (DMSO): 0.63 (t, 6H, J=7.5 Hz); 0.87 (t, 3H, J=7.4 Hz); 1.16–1.24 (m, 6H); 1.90–2.00 (m, 2H); 2.26 (q, 2H, J=7.4 Hz); 3.76 (s, 1H); 4.27 (d, 2H, J=5.3 Hz); 4.36 (d, 2H, J=5.3 Hz); 4.77 (t, 1H, J=5.3 Hz); 4.94 (t, 1H, J=5.3 Hz); 5.03 (s, 2H); 5.62 (t, 1H, J=7.3 Hz); 6.67–6.76 (m, 2H); 6.88 (d, 2H, J=2.5 Hz); 7.12 (d, 1H, J=13.8 Hz).

EXAMPLE 10

(E)-7-[4-[2-(3,4-bis-Hydroxymethyl-phenyl)ethyl]-2-thienyl)-3-ethylnon-6-en-3-ol a) 2-(4-Bromo-2-thienyl)-2-ethyl-[1,3]dioxolane 10.5 g (48 mmol) of 1-(4-bromo-2-thienyl)-1-propanone (described in Example 9(b)) are dissolved in 150 mL of toluene. 13.4 mL (239 mmol) of ethylene glycol and 450 mg (2.4 mmol) of para-toluenesulphonic acid are added. The assembly is equipped with Dean-Stark distillation apparatus and the reaction medium is heated to 130° C. After refluxing for 24 hours, the mixture is treated with sodium bicarbonate solution and extracted with ethyl acetate. The crude product obtained is the desired product (m=12.2 g; Y=100%).

b) 2-(2-Ethyl-[1,3]dioxolan-2-yl)thiophene-4-carbaldehyde

In a manner similar to that of Example 9(g), by reaction of 12 g (45.6 mmol) of 2-(4-bromo-2-thienyl)-2-ethyl-[1,3]dioxolane with 20 mL (50 mmol) of 2.5 M butyllithium and 3.9 mL (50 mmol) of dimethylformamide, the desired product is obtained in the form of a yellow oil (m=4.6 g, Y=48%).

c) Dimethyl 4-{(E)-2-[2-(2-Ethyl-[1,3]dioxolan-2-yl)-4-thienyl]vinyl}phthalate

In a manner similar to that of Example 8(a), by reaction of 4.6 g (21.6 mmol) of 2-(2-ethyl-[1,3]dioxolan-2-yl)thiophene-4-carbaldehyde with 8.9 g (26 mmol) of dimethyl 4-(diethoxyphosphorylmethyl)-phthalate and 2.9 g (26 mmol) of potassium tert-butoxide, the desired product is obtained in the form of a yellow oil (m=7 g; Y=87%).

d) Dimethyl 4-{2-[2-(2-Ethyl-[1,3]dioxolan-2-yl)-4-thienyl]ethyl}phthalate

In a manner similar to that of Example 8(b), by reaction of 7 g (19 mmol) of dimethyl 4-{(E)-2-[2-(2-ethyl-[1,3]dioxolan-4-yl)-3-thienyl]vinyl}phthalate with 7 g of 5% palladium-on-charcoal, the desired product is obtained in the form of a colourless oil (m=6.7 g; Y=95%).

e) (4-{2-[2-(2-Ethyl-[1,3]dioxolan-2-yl)-4-thienyl]-ethyl}-2-hydroxymethylphenyl)methanol In a manner similar to that of Example 6(f), by reaction of 6.7 g (18 mmol) of dimethyl 4-{2-[2-(2-ethyl-[1,3]dioxolan-2-yl)-4-thienyl]ethyl}phthalate with 1.6 g (43 mmol) of lithium aluminium hydride, the desired product is obtained in the form of a colourless oil (m=5.3 g; Y=85%).

f) 1-{4-[2-(3,4-bis-Hydroxymethyl-phenyl)ethyl]-2-thienyl}-1-propanone

In a manner similar to that of Example 6(g), by reaction of 5.3 g (15 mmol) of (4-{2-[2-(2-ethyl-[1,3]dioxolan-2-yl)-4-thienyl]ethyl}-2-hydroxymethyl-phenyl)methanol with a solution of para-toluenesulphonic acid in an acetone/water mixture, the desired product is obtained in the form of a white powder (m=4 g; Y=86%).

g) 1-{4-[2-(3,4-bis(tert-Butyldimethylsilanyloxy-methyl)phenyl)ethyl]-2-thienyl}-1-propanone In a manner similar to that of Example 6(h), by reaction of 3.8 g (12 mmol) of 1-{4-[2-(3,4-bis-hydroxymethyl-phenyl)ethyl]-2-thienyl}-1-propanone with 2.1 g (31 mmol) of imidazole and 4.1 g (27.5 mmol) of tert-butyldimethylchlorosilane, the desired product is obtained in the form of a colourless oil (m=6.8 g; Y=100%).

h) (E)-5-{4-[2-(3,4-bis(tert-Butyldimethylsilanyloxy-methyl)phenyl)ethyl]-2-thienyl}-4-heptenoic Acid In a manner similar to that of Example 6(i), by reaction of 3 g (5.6 mmol) of 1-{4-[2-(3,4-bis(tert-butyldimethylsilanyloxymethyl)phenyl)ethyl]-2-thienyl}-1-propanone with 3.6 g (8.4 mmol) of (3-carboxy-propyl)triphenylphosphonium bromide and 1.9 g (17 mmol) of potassium tert-butoxide, the desired product is obtained in the form of a yellow oil (m=1.7 g, Y=50%).

i) Methyl (E)-5-{4-[2-(3,4-bis(tert-Butyldimethyl-silanyloxymethyl)phenyl)ethyl]-2-thienyl}-4-heptenoate In a manner similar to that of Example 6(j), by reaction of 1.6 g (2.6 mmol) of (E)-5-{4-[2-(3,4-bis(tert-butyldimethylsilanyloxymethyl)phenyl)ethyl]-2-thienyl}-4-heptenoic acid with 400 mg (2.9 mmol) of potassium carbonate and 810 μL (13 mmol) of methyl iodide, the desired product is obtained in the form of a yellow oil (m=1.4 g; Y=86%).

j) (E)-7-{4-[2-(3,4-bis(tert-Butyldimethylsilanyloxy-methyl)phenyl)ethyl]-2-thienyl}-3-ethylnon-6-en-3-ol In a manner similar to that of Example 6(k), by reaction of 1.4 g (2.3 mmol) of methyl (E)-5-{4-[2-(3,4-bis(tert-butyldimethylsilanyloxymethyl)phenyl)-ethyl]-2-thienyl}-4-heptenoate with 3 mL (9 mmol) of 3.0 M ethylmagnesium bromide, the desired product is obtained in the form of a colourless oil (m=1 g, Y=69%).

k) (E)-7-{4-[2-(3,4-bis-Hydroxymethyl-phenyl)ethyl]-2-thienyl}-3-ethylnon-6-en-3-ol In a manner similar to that of Example 6(l), by reaction of 1 g (1.55 mmol) of (E)-7-{4-[2-(3,4-bis(tert-butyldimethylsilanyloxymethyl)phenyl)ethyl]-2-thienyl}-3-ethylnon-6-en-3-ol with 3.7 mL (3.7 mmol) of 1.0 M tetrabutylammonium fluoride solution, the desired product is obtained in the form of white crystals (m.p.=85–86° C.; m=580 mg; Y=90%).

$^1$H NMR (DMSO): 0.89 (t, 6H, J=7.6 Hz); 1.12 (t, 3H, J=7.4 Hz); 1.42–1.51 (m, 6H); 2.15–2.24 (m, 2H); 2.50 (q, 2H, J=7.4 Hz); 2.96–3.01 (m, 2H); 3.08–3.14 (m, 2H); 4.00 (s, 1H); 4.58–4.62 (m, 4H); 5.11 (t, 1H, J=4.7 Hz); 5.15 (t, 1H, J=4.8 Hz); 5.79 (t, 1H, J=7.4 Hz); 6.81 (d, 1H, J=3.5 Hz); 6.90 (d, 1H, J=3.5 Hz); 7.20 (d, 1H, J=7.7 Hz); 7.35–7.38 (m, 2H).

EXAMPLE 11

(E)-7-[5-(3,4-bis-Hydroxymethyl-phenoxymethyl)-3-thienyl]-3-ethyl-4,4-dimethylnon-6-en-3-ol a) (3-Bromo-5-thienyl)methanol In a manner similar to that of Example 9(h), by reaction of 20.5 g (107 mmol) of 3-bromothiophene-3-carboxaldehyde with 4 g (110 mmol) of sodium borohydride, the desired product is obtained in the form of a yellow oil (m=20 g; Y=100%).

b) Dimethyl 3-(3-Bromo-5-thienylmethoxy)phthalate

In a manner similar to that of Example 9(i), by reaction of 20 g (103 mmol) of (3-bromo-5-thienyl)methanol with 21.6 mL (155 mmol) of triethylamine and 8.8 mL (114 mmol) of methanesulphonyl chloride, followed by 500 mg (3.5 mmol) of sodium iodide, 14.3 g (103 mmol) of potassium carbonate and 21.7 g (103 mmol) of dimethyl 4-hydroxyphthalate, the desired product is obtained in the form of orange-coloured crystals (m.p.=65° C.; m=27 g; Y=74%).

c) [5-(3-Bromo-5-thienylmethoxy)-2-hydroxymethyl-phenyl]methanol 27 g (76 mmol) of dimethyl 4-(3-bromo-5-thienylmethoxy)phthalate are dissolved in 200 mL of anhydrous THF. This solution is added dropwise to a suspension of 4 g (183 mmol) of lithium borohydride in 50 mL of THF. The reaction medium is refluxed for 24 h and then cooled and poured onto 200 g of ice. After extraction with ether and then chromatography on a column of silica (eluent: 5 heptane/5 ethyl acetate), the desired product is obtained in the form of a yellow oil (m=22.1 g; Y=88%).

d) 5-[3,4-bis(tert-Butyldimethylsilanyloxymethyl)-phenoxymethyl]-3-bromothiophene In a manner similar to that of Example 6(h), by reaction of 22 g (67 mmol) of [5-(3-bromo-5-thienylmethoxy)-2-hydroxymethylphenyl]methanol with 11.4 g (167 mmol) of imidazole and 22 g (147 mmol) of tert-butyldimethylchlorosilane, the desired product is obtained in the form of a colourless oil (m=34 g, y=91%).

e) 5-[3,4-bis(tert-Butyldimethylsilanyloxymethyl)-phenoxymethyl]thiophene-3-carbaldehyde In a manner similar to that of Example 9(g), by reaction of 34 g (61 mmol) of 5-[3,4-bis(tert-butyldimethylsilanyloxymethyl)phenoxymethyl]-3-bromothiophene with 27 mL (67 mmol) of 2.5 M butyl-lithium and 5.2 mL (67 mmol) of dimethylformamide, the crude product obtained (33.8 g; Y=99%) is in the form of a brown oil.

f) 1-{5-[3,4-bis(tert-Butyldimethylsilanyloxymethyl)-phenoxymethyl]-3-thienyl}-1-propanol In a manner similar to that of Example 9(a), by reaction of 33 g (65 mmol) of 5-[3,4-bis(tert-butyldimethylsilanyloxymethyl)phenoxymethyl]thiophene-3-carbaldehyde with 44 mL (130 mmol) of ethylmagnesium bromide, the product is obtained in the form of a yellow oil (m=28.4 g; Y=88%).

g) 1-{5-[3,4-bis(tert-Butyldimethylsilanyloxymethyl)-phenoxymethyl]-3-thienyl}-1-propanone In a manner similar to that of Example 9(b), by reaction of 28 g (52 mmol) of 1{5-[3,4-bis(tert-butyldimethylsilanyloxymethyl)phenoxymethyl]-3-thienyl}-1-propanol with 45 g (520 mmol) of manganese dioxide, the desired product is obtained in the form of an orange-coloured oil (m=26 g; Y=93%).

h) (E)-5-{5-[3,4-bis(tert-Butyldimethylsilanyloxy-methyl)phenoxymethyl]-3-thienyl}-4-heptenoic Acid In a manner similar to that of Example 6(i), by reaction of 10 g (18.7 mmol) of 1-{5-[3,4-bis(tert-butyldimethylsilanyloxymethyl)phenoxymethyl]-3-thienyl}-1-propanone with 12 g (28 mmol) of (3-carboxy-propyl)triphenylphosphonium bromide and 6.3 g (56 mmol) of potassium tert-butoxide, the desired product is obtained in the form of a brown oil (m=5.4 g; Y=48%).

i) Methyl (E)-5-{5-[3,4-bis(tert-Butyldimethyl-silanyloxymethyl)phenoxymethyl]-3-thienyl}-4-heptenoate In a manner similar to that of Example 6(j), by reaction of 5.4 g (8.9 mmol) of (E)-5-{5-[3,4-bis(tert-butyldimethylsilanyloxymethyl)phenoxymethyl]-3-thienyl}-4-heptenoic acid with 1.3 g (9.4 mmol) of potassium carbonate and 2.7 mL (44 mmol) of methyl iodide, the desired product is obtained in the form of a colourless oil (m=3 g; Y=54%).

j) Methyl (E)-5-{5-[3,4-bis(tert-Butyldimethylsilanyloxymethyl)phenoxymethyl]-3-thienyl}-2,2-dimethyl-4-heptenoate 1.3 g (2.1 mmol) of methyl (E)-5-{5-[3,4-bis(tert-butyldimethylsilanyloxymethyl)phenoxymethyl]-3-thienyl}-4-heptenoate are dissolved in 20 mL of THF. This solution is added to a solution of 3.2 mmol of lithium diisopropylamide in 10 mL of THF at −78° C. After 10 minutes, 390 μL (6.2 mmol) of methyl iodide are added and the reaction medium is warmed to room temperature and then stirred for 12 h. After the usual treatment, the crude residue obtained is subjected a second time to the same operating conditions. After chromatography on silica gel (eluent: 97 heptane/3 ethyl acetate), the desired product is obtained in the form of a colourless oil (m=680 mg; Y=50%).

k) (E)-7-{5-[3,4-bis(tert-Butyldimethylsilanyloxy-methyl)phenoxymethyl]-3-thienyl}-3-ethyl-4,4-dimethylnon-6-en-3-ol In a manner similar to that of Example 6(k), by reaction of 670 mg (1 mmol) of methyl (E)-5-{5-[3,4-bis(tert-butyldimethylsilanyloxymethyl)phenoxymethyl]-3-thienyl}-2,2-dimethyl-4-heptenoate with 1.4 mL (4.2 mmol) of ethylmagnesium bromide, the desired product is obtained in the form of a colourless oil (m=310 mg; Y=44%).

l) (E)-7-[5-(3,4-bis-Hydroxymethyl-phenoxymethyl)-3-thienyl]-3-ethyl-4,4-dimethylnon-6-en-3-ol In a manner similar to that of Example 6(l), by reaction of 310 mg (0.46 mmol) of (E)-7-{5-[3,4-bis(tert-butyldimethylsilanyloxymethyl)phenoxymethyl]-3-thienyl}-3-ethyl-4,4-dimethylnon-6-en-3-ol with 1.1 mL (1.1 mmol) of 1.0 M tetrabutylammonium bromide, the desired product is obtained in the form of a colourless oil (m=200 mg; Y=98%).

$^1$H NMR (CDCl$_3$): 0.93–1.08 (m, 12H); 1.22 (t, 3H, J=8.6 Hz); 1.62 (q, 4H, J=8.5 Hz); 2.29 (d, 2H, J=9.6 Hz); 2.48 (q, 2H, J=8.6 Hz); 4.71 (s, 2H); 4.73 (s, 2H); 5.20 (s, 2H); 5.94 (t, 1H, J=9.6 Hz); 6.90–6.95 (m, 1H); 7.04 (d, 1H, J=3.9 Hz); 7.09 (d, 1H, J=3.8 Hz); 7.22–7.31 (m, 2H).

EXAMPLE 12

(E)-7-[5-(3,4-bis-Hydroxymethyl-phenoxymethyl)-3-thienyl]-3-ethylnon-6-en-3-ol a) (E)-7-{5-[3,4-bis(tert-Butyldimethylsilanyloxy-methyl)phenoxymethyl]-3-thienyl}-3-ethylnon-6-en-3-ol In a manner similar to that of Example 6(k), by reaction of 1 g (1.6 mmol) of methyl (E)-5-{5-[3,4-bis(tert-butyldimethylsilanyloxymethyl)phenoxymethyl]-3-thienyl}-4-heptenoate (described in Example 11(i)) with 2.1 mL (6.3 mmol) of 3.0 M ethylmagnesium bromide, the desired product is obtained in the form of a colourless oil (m=1 g; Y=96%).

b) (E)-7-[5-(3,4-bis-Hydroxymethyl-phenoxymethyl)-3-thienyl]-3-ethylnon-6-en-3-ol In a manner similar to that of Example 6(l), by reaction of 1 g (1.5 mmol) of (E)-7-{5-[3,4-bis(tert-butyldimethylsilanyloxymethyl)phenoxymethyl]-3-thienyl}-3-ethylnon-6-en-3-ol with 3.7 mL (3.7 mmol) of 1.0 M tetrabutylammonium bromide, the desired product is obtained in the form of white crystals (m.p.=73–74° C.; m=480 mg; Y=74%).

$^1$H NMR (DMSO): 0.65 (t, 6H, J=7.6 Hz); 0.84 (t, 3H, J=7.5 Hz); 1.18–1.28 (m, 6H); 1.91–2.00 (m, 2H); 2.25 (q, 2H, J=7.4 Hz); 3.76 (s, 1H); 4.28 (d, 2H, J=4.9 Hz); 4.37 (d, 2H, J=4.9 Hz); 4.79 (t, 1H, J=5.0 Hz); 4.96 (t, 1H, J=5.0 Hz); 5.06 (s, 2H); 5.67 (t, 1H, J=7.3 Hz); 6.69–6.74 (m, 1H); 6.90 (d, 1H, J=2.4 Hz); 7.10 (d, 1H, J=8.3 Hz); 7.17–7.20 (m, 2H).

EXAMPLE 13

(3E,5E)-6-[5-(3,4-bis-Hydroxymethyl-phenoxymethyl)-2-thienyl]-1,1,1-trifluoro-2-trifluoromethylocta-3,5-dien-2-ol a) 2-[3,4-bis(tert-Butyldimethylsilanyloxy-methyl)phenoxymethyl]-5-((E)-4,4-dibromo-1-ethylbuta-1,3-dienyl)thiophene 770 mg (11.7 mmol) of zinc, 3.09 g (11.7 mmol) of triphenylphosphine and 3.9 g (11.7 mmol) of carbon tetrabromide are stirred for 30 minutes at room temperature in 150 mol of dichloromethane. A solution of 3.3 g (5.9 mmol) of (E)-3-{5-[3,4-bis(tert-butyldimethylsilanyloxymethyl)phenoxymethyl]-2-thienyl}pent-2-enal (described in Example 7(c)) in 30 mL of dichloromethane is then added dropwise. After stirring for 1 h at room temperature the reaction medium is treated with water and extracted with dichloromethane. After purification on silica gel (eluent: 95 heptane/5 ethyl acetate), the desired product is obtained in the form of a brown oil (m=3.9 g; Y=93%).

b) 2-[3,4-bis(tert-Butyldimethylsilanyloxy-methyl)phenoxymethyl]-5-((E)-1-ethylbut-1-en-3-ynyl)-thiophene 3.9 g (5.4 mmol) of 2-[3,4-bis(tert-butyldimethylsilanyloxymethyl)phenoxymethyl]-5-((E)-4,4-dibromo-1-ethylbuta-1,3-dienyl)thiophene are dissolved in 100 mL of THF and the mixture is cooled to −78° C. 4.4 mL (11 mmol) of 2.5 M butyllithium are added slowly and the reaction medium is stirred at the same temperature for 1 hour. After the usual treatment and chromatography on silica gel (eluent: 96 heptane/4 ethyl acetate), the desired product is obtained in the form of a brown oil.

c) (E)-6-{5-[3,4-bis(tert-Butyldimethylsilanyloxy-methyl)phenoxymethyl]-2-thienyl}-1,1,1-trifluoro-2-trifluoromethyloct-5-en-3-yn-2-ol 1.7 g (3 mmol) of 2-[3,4-bis(tert-butyldimethylsilanyloxymethyl)phenoxymethyl]-5-((E)-1-ethyl-but-1-en-3-ynyl)thiophene are dissolved in 50 mL of THF and the mixture is cooled to −78° C. 1.3 mL (3.3 mmol) of 2.5 M butyllithium are then added. After stirring for 15 minutes at the same temperature, a gentle flow of hexafluoroacetone (gas) is introduced into the reaction medium. After reaction for 20 minutes at −78° C., the flow of gas is stopped and the reaction medium is treated in the usual manner. The residue obtained is purified by chromatography on silica gel. The desired product is obtained in the form of a yellow oil (1 g).

d) (3E,5E)-6-{5-[3,4-bis(tert-Butyldimethylsilanyl-oxymethyl)phenoxymethyl]-2-thienyl}-1,1,1-trifluoro-2-trifluoromethylocta-3,5-dien-2-ol 1 g (1.3 mmol) of (E)-6-{5-[3,4-bis(tert-butyldimethylsilanyloxymethyl)phenoxymethyl]-2-thienyl}-1,1,1,-trifluoro-2-trifluoromethyloct-5-en-3-yn-2-ol is dissolved in 10 mL of THF and then added to a suspension of 160 mg (4.2 mmol) of lithium aluminium hydride and 450 mg (8.4 mmol) of sodium methoxide in 20 mL of THF. After stirring at reflux for 2 hours, the medium is cooled and then treated with 200 μL of water, 200 μL of 15% sodium hydroxide and 600 μL of water. After filtration, the residue is purified by chromatography on silica gel (eluent: 95 heptane/5 ethyl acetate). The desired product is obtained in the form of a yellow oil (210 mg).

e) (3E,5E)-6-[5-(3,4-bis-Hydroxymethyl-phenoxymethyl)-2-thienyl]-1,1,1-trifluoro-2-trifluoromethylocta-3,5-dien-2-ol In a manner similar to that of Example 6(l), by reaction of 200 mg of (3E,5E)-6-{5-[3,4-bis(tert-butyldimethylsilanyloxymethyl)phenoxymethyl]-2-thienyl}-1,1,1-trifluoro-2-trifluoromethylocta-3,5-dien-2-ol with 700 μL (0.7 mmol) of 1.0 M tetrabutylammonium bromide, the desired product is obtained in the form of white crystals (m.p.=113–114° C.; m=70 mg).

$^1$H NMR (DMSO): 1.12 (t, 3H, J=7.5 Hz); 2.71 (q, 2H, J=7.5 Hz); 4.48 (d, 2H, J=5.1 Hz); 4.57 (d, 2H, J=5.1 Hz); 4.99 (t, 1H, J=5.1 Hz); 5.15 (t, 1H, J=5.1 Hz); 5.29 (s, 2H); 5.53 (d, 1H, J=11.6 Hz); 6.89–7.04 (m, 2H); 7.10–7.35 (m, 5H); 8.50 (s, 1H).

EXAMPLE 14

(4E,6E)-7-[5-(3,4-bis-Hydroxymethyl-phenoxymethyl)-3-thienyl]-3-ethylnona-4,6-dien-3-ol a) Ethyl (E)-3-{5-[3,4-bis(tert-Butyldimethyl-silanyloxymethyl)phenoxymethyl]-3-thienyl}-2-pentenoate In a manner similar to that of Example 7(a), by reaction of 6 g (11.2 mmol) of 1-{5-[3,4-bis(tert-butyldimethylsilanyloxymethyl)phenoxymethyl]-3-thienyl}-1-propanone (prepared in Example 11(g)) with 4.4 mL (22.4 mol) of triethyl phosphonoacetate and 0.9 g (22.4 mmol) of sodium hydride, the desired product is separated from its Z isomer and obtained in the form of a colourless oil (m=5.3 g; Y=78%).

b) (E)-3-{5-[3,4-bis(tert-Butyldimethylsilanyloxy-methyl)phenoxymethyl]-3-thienyl}pent-2-en-1-ol In a manner similar to that of Example 7(b), by reaction of 2.3 g (3.8 mmol) of ethyl (E)-3-{5-[3,4-bis(tert-butyldimethylsilanyloxymethyl)phenoxymethyl]-3-thienyl}-2-pentenoate with 180 mg (4.7 mmol) of lithium aluminium hydride, the desired product (m=2.1 g; Y=100%) is obtained in the form of a colourless oil.

c) (E)-3-{5-[3,4-bis(tert-Butyldimethylsilanyloxy-methyl)phenoxymethyl]-3-thienyl}pent-2-enal In a manner similar to that of Example 7(c), by reaction of 2.1 g (3.7 mmol) of (E)-3-{5-[3,4-bis(tert-butyldimethylsilanyloxymethyl)phenoxymethyl]-3-thienyl}pent-2-en-1-ol with 4.9 g (56 mmol) of manganese dioxide, the crude product (1.8 g) is the expected aldehyde, obtained in a yield of 86%.

d) Ethyl (2E,4E)-5-{5-[3,4-bis(tert-Butyldimethylsilanyloxymethyl)phenoxymethyl]-3-thienyl}hepta-2,4-dienoate In a manner similar to that of Example 7(a), by reaction of 1.8 g (3.2 mmol) of (E)-3-{5-[3,4-bis(tert-butyldimethylsilanyloxymethyl)phenoxymethyl]-3-thienyl}pent-2-enal with 0.96 mL (4.8 mmol) of triethyl phosphonoacetate, a single isomer is obtained: ethyl (2E,4E)-5-{5-[3,4-bis(tert-butyldimethyl-silanyloxymethyl)phenoxymethyl]-3-thienyl}hepta-2,4-dienoate is isolated in the form of a yellow oil (m=2 g; Y=100%).

e) (4E,6E)-7-{5-[3,4-bis(tert-Butyldimethylsilanyl-oxymethyl)phenoxymethyl]-3-thienyl}-3-ethylnona-4,6-dien-3-ol In a manner similar to that of Example 7(e), by reaction of 1.6 g (2.5 mmol) of ethyl (2E,4E)-5-{5-[3,4-bis(tert-butyldimethylsilanyloxymethyl)phenoxymethyl]-3-thienyl}hepta-2,4-dienoate with 17 mL of ethyllithium solution (1.5 M), the desired product is obtained in the form of a yellow oil (m=160 mg, Y=10%).

f) (4E,6E)-7-[5-(3,4-bis-Hydroxymethyl-phenoxymethyl)-3-thienyl]-3-ethylnona-4,6-dien-3-ol In a manner similar to that of Example 7(f), by reaction of 155 mg (0.24 mmol) of (4E,6E)-7-{5-(3,4-bis(tert-butyldimethylsilanyloxymethyl)phenoxymethyl]-3-thienyl}-3-ethylnona-4,6-dien-3-ol with 0.58 mL (0.58 mmol) of 1 M tetrabutylammonium fluoride solution, (4E,6E)-7-[5-(3,4-bis-hydroxymethyl-phenoxymethyl)-3-thienyl]-3-ethylnona-4,6-dien-3-ol is obtained in the form of a yellow oil (m=80 mg; Y=80%).

$^1$H NMR (DMSO): 0.83 (t, J=7.5 Hz, 6H); 1.08 (t, J=7.6 Hz, 3H); 1.50 (q, J=7.5 Hz, 4H); 2.54–2.60 (m, 2H); 4.33 (s, 1H); 4.48 (d, J=5 Hz, 2H); 4.57 (d, J=5 Hz, 2H); 4.98 (t, J=5 Hz, 1H); 5.15 (t, J=5 Hz, 1H); 5.27 (s, 2H); 5.80–5.84 (m, 1H); 6.55–6.59 (m, 2H); 6.91 (dd, $J_1$=2.6 Hz, $J_2$=8.3 Hz, 1H); 7.10 (d, J=2.6 Hz, 1H); 7.29 (d, J=8.2 Hz, 1H); 7.49 (s, 2H).

EXAMPLE 15

(4E,6E)-7-{4-[2-(3,4-bis-Hydroxymethyl-phenyl)ethyl]-thiopen-2-yl}-3-ethylnona-4,6-dien-3-ol a) Ethyl (E)-3-(4-{2-[3,4-bis(tert-Butyldimethyl-silanyloxymethyl)phenyl]ethyl}-2-thienyl)-2-pentenoate In a manner similar to that of Example 7(a), by reaction of 3.6 g (6.7 mmol) of (E)-1-{4-[2-(3,4-bis(tert-butyldimethylsilanyloxymethyl)phenyl)ethyl]-2-thienyl}-1-propanone (prepared in Example 10(g)) with 2.7 mL (13.5 mmol) of triethyl phosphonoacetate and 540 mg (13.5 mmol) of sodium hydride, the desired product is separated from its Z isomer and obtained in the form of a colourless oil (m=3.5 g; Y=86%).

b) (E)-3-(4-{2-[3,4-bis(tert-Butyldimethyl-silanyloxymethyl)phenyl]ethyl}-2-thienyl)pent-2-en-1-ol In a manner similar to that of Example 7(b), by reaction of 2.3 g (3.8 mmol) of ethyl (E)-3-(4-{2-[3,4-bis(tert-butyldimethylsilanyloxymethyl)phenyl]ethyl}-2-thienyl)-2-pentenoate with 180 mg (4.7 mmol) of lithium aluminium hydride, the desired product (m=2.1 g; Y=100%) is obtained in the form of a colourless oil.

c) (E)-3-(4-{2-[3,4-bis(tert-Butyldimethyl-silanyloxymethyl)phenyl]ethyl}-2-thienyl)pent-2-enal In a manner similar to that of Example 7(c), by reaction of 2.0 g (3.6 mmol) of (E)-3-(4-{2-[3,4-bis(tert-Butyldimethylsilanyloxymethyl)phenyl]ethyl}-2-thienyl)pent-2-en-1-ol with 4.9 g (56 mmol) of manganese dioxide, the crude product (2.0 g) is the expected aldehyde, obtained in quantitative yield.

d) Ethyl (2E,4E)-5-(4-{2-[3,4-bis(tert-Butyldimethyl-silanyloxymethyl)phenyl]ethyl}-2-thienyl)hepta-2,4-dienoate In a manner similar to that of Example 7(d), by reaction of 2 g (3.6 mmol) of (E)-3-(4-{2-[3,4-bis(tert-butyldimethylsilanyloxymethyl)phenyl]ethyl}-2-thienyl)pent-2-enal with 1.1 mL (5.4 mmol) of triethyl phosphonoacetate, a single isomer is obtained: ethyl (2E,4E)-5-(4-{2-[3,4-bis(tert-butyldimethyl-silanyloxymethyl)phenyl]ethyl}-2-thienyl)hepta-2,4-dienoate is isolated in the form of a yellow oil (m=1.9 g; Y=85%).

e) (4E,6E)-7-(4-{2-[3,4-bis(tert-Butyldimethyl-silanyloxymethyl)phenyl]ethyl}-2-thienyl)-3-ethyl-nona-4,6-dien-3-ol In a manner similar to that of Example 7(e), by reaction of 1.9 g (3 mmol) of ethyl (2E,4E)-5-(4-{2-[3,4-bis(tert-butyldimethylsilanyloxymethyl)phenyl]-ethyl}-2-thienyl)hepta-2,4-dienoate with 20 mL of ethyllithium solution (1.5 M), the desired product is obtained in the form of a yellow oil (m=448 mg, Y=24%).

f) (4E,6E)-7-(4-{2-[3,4-bis-Hydroxymethyl-phenyl]-ethyl}-2-thienyl)-3-ethylnona-4,6-dien-3-ol In a manner similar to that of Example 7(f), by reaction of 440 mg (0.68 mmol) of (4E,6E)-7-(4-{2-[3,4-bis(tert-butyldimethylsilanyloxymethyl)phenyl]ethyl}-2-thienyl)-3-ethylnona-4,6-dien-3-ol with 1.5 mL (1.5 mmol) of 1 M tetrabutylammonium fluoride solution, (4E,6E)-7-(4-{2-[3,4-bis-hydroxymethyl-phenyl]ethyl}-2-thienyl)-3- ethylnona-4,6-dien-3-ol is obtained in the form of a yellow oil (m=200 mg; Y=71%).

$^1$H NMR (DMSO): 0.57 (t, J=7.5 Hz, 6H); 0.88 (t, J=7.6 Hz, 3H); 1.24 (q, J=7.5 Hz, 6H); 2.29–2.34 (m, 2H); 2.66–2.72 (m, 2H); 2.79–2.85 (m, 2H); 4.07 (s, 1H); 4.27–4.31 (m, 4H); 4.79 (t, J=5 Hz, 1H); 4.83 (t, J=5 Hz, 1H); 5.54 (d, J=14.7 Hz, 1H); 6.13 (d, J=11.1 Hz, 1H); 6.28 (dd, J$_1$=11.1 Hz, J$_2$=14.7 Hz, 1H); 6.54 (d, J=3.6 Hz, 1H); 6.72 (d, J=3.6 Hz, 1H); 6.88 (dd, J$_1$=1.4 Hz, J$_2$=6.3 Hz, 1H); 7.05–7.07 (m, 2H).

EXAMPLE 16

Formulation Examples

1) Oral Route (a) The composition below is prepared in the form of a 0.2 g tablet:

| | |
|---|---|
| Compound of Example 1 | 0.005 g |
| Pregelatinized starch | 0.065 g |
| Microcrystalline cellulose | 0.075 g |
| Lactose | 0.050 g |
| Magnesium stearate | 0.005 g |

For the treatment of ichthyosis, 1 to 3 tablets per day are administered to an adult individual for 1 to 12 months depending on the severity of the case treated.

(b) A drinkable suspension, intended to be packaged in 5 mL ampules, is prepared:

| | |
|---|---|
| Compound of Example 2 | 0.050 mg |
| Glycerol | 0.500 g |
| 70% sorbitol | 0.500 g |
| Sodium saccharinate | 0.010 9 |
| Methyl para-hydroxybenzoate | 0.040 g |
| Flavouring q.s. | |
| Purified water q.s. | 5 mL |

For the treatment of acne, 1 ampule per day is administered to an adult individual for 1 to 12 months depending on the severity of the case treated.

(c) The formulation below intended to be packaged in gel capsules is prepared:

| | |
|---|---|
| Compound of Example 4 | 0.0001 mg |
| Corn starch | 0.060 g |
| Lactose q.s. | 0.300 g |

The gel capsules used consist of gelatin, titanium oxide and a preserving agent.

In the treatment of psoriasis, 1 gel capsule per day is administered to an adult individual for 1 to 12 months.

(d) The formulation below intended to be packed in gel capsules is prepared:

| | |
|---|---|
| Compound of Example 5 | 0.02 mg |
| Cyclosporin | 0.050 g |
| Corn starch | 0.060 g |
| Lactose q.s. | 0.300 g |

The gel capsules used consist of gelatin, titanium oxide and a preserving agent.

In the treatment of psoriasis, 1 gel capsule per day is administered to an adult individual for 1 to 12 months.

2) Topical Route (a) The nonionic water-in-oil cream below is prepared:

| | |
|---|---|
| Compound of Example 10 | 0.100 g |
| Mixture of emulsifying lanolin alcohols, waxes and refined oils, sold by the company BDF under the name "Anhydrous eucerin" | 39.900 g |
| Methyl para-hydroxybenzoate | 0.075 g |
| Propyl para-hydroxybenzoate | 0.075 g |
| Sterile demineralized water q.s. | 100.000 g |

This cream is applied to skin afflicted with psoriasis 1 to 2 times a day for 1 to 12 months.

(b) A gel is prepared by preparing the formulation below:

| | |
|---|---|
| Compound of Example 15 | 0.001 g |
| Erythromycin base | 4.000 g |
| Butylhydroxytoluene | 0.050 g |
| Hydroxypropylcellulose sold by the company Hercules under the name "Klucel HF" | 2.000 g |
| Ethanol (at 95°) q.s. | 100.000 g |

This gel is applied to skin afflicted with dermatitis or with acne 1 to 3 times a day for 6 to 12 weeks depending on the severity of the case treated.

(c) An antiseborrhoeic lotion is prepared by mixing together the following ingredients:

| | |
|---|---|
| Compound of Example 12 | 0.030 g |
| Propylene glycol | 5.000 g |
| Butylhydroxytoluene | 0.100 g |
| Ethanol (at 95°) q.s. | 100.000 g |

This lotion is applied twice a day to a seborrhoeic scalp and a significant improvement is observed within a period of 2 to 6 weeks.

(d) A cosmetic composition to combat the harmful effects of sunlight is prepared by mixing together the following ingredients:

| | |
|---|---|
| Compound of Example 8 | 1.000 g |
| Benzylidenecamphor | 4.000 g |
| Fatty acid triglycerides | 31.000 g |
| Glyceryl monostearate | 6.000 g |
| Stearic acid | 2.000 g |
| Cetyl alcohol | 1.200 g |
| Lanolin | 4.000 g |
| Preserving agents | 0.300 g |
| Propylene glycol | 2.000 g |
| Triethanolamine | 0.500 g |
| Fragrance | 0.400 g |
| Demineralized water q.s. | 100.000 g |

This composition is applied daily and helps to combat light-induced ageing.

(e) The nonionic oil-in-water cream below is prepared:

| | |
|---|---|
| Compound of Example 7 | 0.500 g |
| Retinoic acid | 0.020 g |
| Cetyl alcohol | 4.000 g |

| | |
|---|---|
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water q.s. | 100.000 g |

This cream is applied to skin afflicted with psoriasis, 1 to 2 times a day for 30 days for an attacking treatment, and indefinitely for a maintenance treatment.

(f) A topical gel is prepared by mixing together the following ingredients:

| | |
|---|---|
| Compound of Example 11 | 0.050 g |
| Ethanol | 43.000 g |
| α-Tocopherol | 0.050 g |
| Carboxyvinyl polymer sold under the name "Carbopol 941" by the company "Goodrich" | 0.500 g |
| Triethanolamine as an aqueous solution at 20% by weight | 3.800 g |
| Water | 9.300 g |
| Propylene glycol q.s. | 100.000 g |

This gel is applied in the treatment of acne 1 to 3 times a day for 6 to 12 weeks depending on the severity of the case treated.

(g) A lotion for preventing hair loss and for promoting regrowth of the hair is prepared by mixing together the following ingredients:

| | |
|---|---|
| Compound of Example 14 | 0.05 g |
| Compound sold under the name "Minoxidil" | 1.00 g |
| Propylene glycol | 20.00 g |
| Ethanol | 34.92 g |
| Polyethylene glycol (molecular mass = 400) | 40.00 g |
| Butylhydroxyanisole | 0.01 g |
| Butylhydroxytoluene | 0.02 g |
| Water q.s. | 100.00 g |

This lotion is applied 1 to 2 times a day for 3 months to a scalp which has suffered hair loss, and indefinitely for a maintenance treatment.

(h) An anti-acne cream is prepared by mixing together the following ingredients:

| | |
|---|---|
| Compound of Example 5 | 0.050 g |
| Retinoic acid | 0.010 g |
| Mixture of glyceryl stearate and polyethylene glycol stearate (75 mol) sold under the name "Gelot 64" by the company "Gattefosse" | 15.000 g |
| Polyoxyethylenated kernel oil containing 6 mol of ethylene oxide, sold under the name "Labrafil M2130 CS" by the company "Gattefosse" | 8.000 g |
| Perhydrosqualene | 10.000 g |
| Preserving agents | q.s. |
| Polyethylene glycol (molecular mass = 400) | 8.000 g |
| Disodium salt of ethylenediamine tetraacetic acid | 0.050 g |
| Purified water q.s. | 100.000 g |

This cream is applied to skin afflicted with dermatitis or acne 1 to 3 times a day for 6 to 12 weeks.

(i) An oil-in-water cream is prepared by preparing the following formulation:

| | |
|---|---|
| Compound of Example 4 | 0.020 g |
| Betamethasone 17-valerate | 0.050 g |
| S-carboxymethylcysteine | 3.000 g |
| Polyoxyethylene stearate (40 mol of ethylene oxide) sold under the name "Myrj 52" by the company "Atlas" | 4.000 g |
| Sorbitan monolaurate polyoxyethylenated with 20 mol of ethylene oxide, sold under the name "Tween 20" by the company "Atlas" | 1.800 g |
| Mixture of glyceryl mono- and distearate sold under the name "Géléol" by the company "Gattefosse" | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preserving agents | q.s. |
| Perhydrosqualene | 18.000 g |
| Mixture of caprylic/capric triglyerides sold under the name "Miglyol 812" by the company "Dynamit Nobel" | 4.000 g |
| Triethanolamine (99% by weight) | 2.500 g |
| Water q.s. | 100.000 g |

This cream is applied twice a day to skin afflicted with inflammatory dermatitis, for 30 days.

(j) The oil-in-water cream below is prepared:

| | |
|---|---|
| Lactic acid | 5.000 g |
| Compound of Example 1 | 0.020 g |
| Polyoxyethylene stearate (40 mol of ethylene oxide) sold under the name "Myrj 52" by the company "Atlas" | 4.000 g |
| Sorbitan monolaurate polyoxyethylenated with 20 mol of ethylene oxide, sold under the name "Tween 20" by the company "Atlas" | 1.800 g |
| Mixture of glyceryl mono- and distearate sold under the name "Geleol" by the company "Gattefosse" | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preserving agents | q.s. |
| Perhydrosqualene | 18.000 g |
| Mixture of caprylic/capric triglyerides sold under the name "Miglyol 812" by the company "Dynamit Nobel" | 4.000 g |
| Water q.s. | 100.000 g |

This cream is applied once a day, and helps to combat ageing, whether light-induced or chronological.

(k) The anhydrous ointment below is prepared:

| Compound of Example 1 | 5.000 g |
|---|---|
| Liquid petroleum jelly | 50.00 g |
| Butylhydroxytoluene | 0.050 g |
| White petroleum jelly | q.s. 100 g |

This ointment is applied twice a day for 30 days to skin afflicted with squamous dermatitis.

3) Intralesional Route (a) The following composition is prepared:

| Compound of Example 2 | 0.002 g |
|---|---|
| Ethyl oleate | q.s. 10 g |

In the treatment of malignant melanoma, the composition is injected into an adult individual at a frequency of 1 to 7 times a week for 1 to 12 months.

(b) The following composition is prepared:

| Compound of Example 1 | 0.050 g |
|---|---|
| Olive oil | q.s. 2 g |

In the treatment of basocellular carcinoma, the composition is injected into an adult individual at a frequency of 1 to 7 times a week for 1 to 12 months.

(c) The following composition is prepared:

| Compound of Example 3 | 0.1 mg |
|---|---|
| Sesame oil | q.s. 2 g |

In the treatment of spinocellular carcinoma, the composition is injected into an adult individual at a frequency of 1 to 7 times a week for 1 to 12 months.

(d) The following composition is prepared:

| Compound of Example 4 | 0.001 mg |
|---|---|
| Methyl benzoate | q.s. 10 g |

In the treatment of carcinoma of the colon, the composition is injected into an adult individual at a frequency of 1 to 7 times a week for 1 to 12 months.

4) Intravenous Route (a) The injectable lipid emulsion below is prepared:

| Compound of Example 4 | 0.001 mg |
|---|---|
| Soyabean oil | 10.000 g |
| Egg phospholipid | 1.200 g |
| Glycerol | 2.500 g |
| Water for injection q.s. | 100.000 g |

In the treatment of psoriasis, the composition is injected into an adult individual at a frequency of 1 to 7 times a week for 1 to 12 months.

(b) The injectable lipid emulsion below is prepared:

| Compound of Example 3 | 0.010 g |
|---|---|
| Cotton Oil | 10.000 g |
| Soyabean lecithin | 0.750 g |
| Sorbitol | 5.000 g |
| D,L-α-tocopherol | 0.100 g |
| Water for injection q.s. | 100.000 g |

In the treatment of ichthyosis, the composition is injected into an adult individual at a frequency of 1 to 7 times a week for 1 to 12 months.

(c) The injectable lipid emulsion below is prepared:

| Compound of Example 2 | 0.001 g |
|---|---|
| Soyabean oil | 15.000 g |
| Acetylated monoglycerides | 10.000 g |
| Pluronic F-108 | 1.000 g |
| Glycerol | 2.500 g |
| Water for injection q.s. | 100.000 g |

In the treatment of leukaemia, the composition is injected into an adult individual at a frequency of 1 to 7 times a week for 1 to 12 months.

(d) The mixed micellar composition below is prepared:

| Compound of Example 2 | 0.001 g |
|---|---|
| Lecithin | 16.930 g |
| Glycocholic acid | 8.850 g |
| Water for injection q.s. | 100.000 g |

In the treatment of malignant melanoma, the composition is injected into an adult individual at a frequency of 1 to 7 times a week for 1 to 12 months.

(e) The cyclodextrin composition below is prepared:

| Compound of Example 1 | 0.1 mg |
|---|---|
| β-Cyclodextrin | 0.100 g |
| Water for injection q.s. | 10.000 g |

In the treatment of graft rejection, the composition is injected into an adult individual at a frequency of 1 to 7 times a week for 1 to 12 months.

(f) The cyclodextrin composition below is prepared:

| Compound of Example 4 | 0.010 g |
|---|---|
| 2-Hydroxypropyl-β-cyclodextrin | 0.100 g |
| Water for injection q.s. | 10.000 g |

In the treatment of cancer of the kidney, the composition is injected into an adult individual at a frequency of 1 to 7 times a week for 1 to 12 months.

EXAMPLE 17

Test Example to Evaluate the Biological Activity of the Compounds of the Invention The VDR agonist activity was tested on the HeLa cell line, by co-transfection of an expression vector of the human VDR receptor and of the reporter plasmid p240Hase-CAT which contains the region −1399 to +76 of the rat 24-hydroxylase promoter, cloned upstream of the coding frame of the chloramphenicol-acetyl-transferase (CAT) gene. 18 hours after co-transfection, the test product is added to the medium. After treatment for 18 hours, the CAT activity of the cell lysates is assayed by an ELISA test. The results are expressed as a percentage of the effect normally observed with $10^{-7}$ M of calcitriol.

The agonist activity was characterized in this co-transfection system by determining the dose required to achieve 50% of the maximum activity of the product (AC50).

| Test Compound | AC 50 (nM) |
|---|---|
| Example 1 | 192 |
| Example 2 | 267 |
| Example 4 | 294 |
| Example 6 | 61 |
| Example 7 | 17 |
| Example 8 | 29 |
| Example 10 | 23 |
| Example 12 | 655 |
| Example 13 | 78 |

What is claimed is:

1. A compound of formula (I):

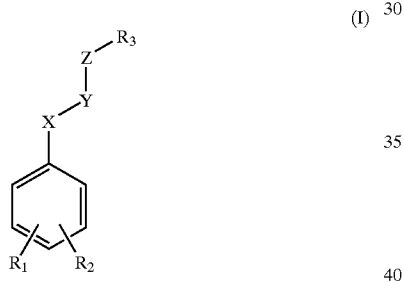

(I)

in which:

$R_1$ represents a hydrogen atom, a $CH_3$ radical or a radical $-(CH_2)_s-OR_4$, $R_2$ represents a radical $-(CH_2)_t-OR_5$, s, t, $R_4$ and $R_5$ having the meanings given below, X—Y represents a bonding group selected from the bonding groups of formulae (a) to (i) below:

 (a)

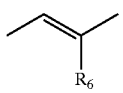 (b)

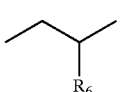 (c)

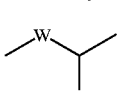 (d)

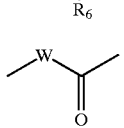 (e)

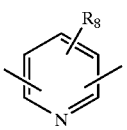 (f)

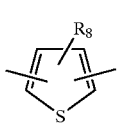 (g)

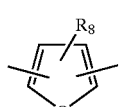 (h)

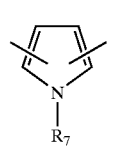 (i)

$R_6$ and W having the meanings given below,

Z represents a ring selected from the rings of formulae (j) to (n) below:

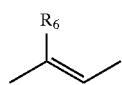 (j)

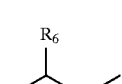 (k)

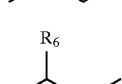 (l)

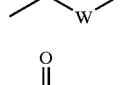 (m)

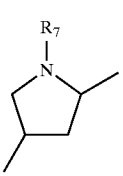 (n)

$R_7$ and $R_8$ having the meanings given below, it being understood that when Z represents the rings of formula (k), (l) or (m), then X—Y cannot represent a bonding group of formula (c) or (d), it being understood that when Z represents a ring of formula (n), then X—Y represents a bonding group of formula (c) or (d), $R_3$ represents an alkyl chain containing from 4 to 8 carbon atoms substituted with one or more hydroxyl groups, it being possible for the hydroxyl groups to be protected in the form of acetoxy, methoxy or ethoxy, trimethylsilyloxy, tert-butyldimethylsilyloxy, tetrahydropyranyloxy and optionally also:

substituted with one or more lower alkyl or cycloalkyl groups and/or substituted with one or more halogen atoms and/or substituted with one or more $CF_3$ groups and/or in which one or more carbon atoms of the chain are replaced with oxygen, sulphur or nitrogen atoms, it being possible for the nitrogen atoms to be optionally substituted with lower alkyl radicals and/or in which one or more single bonds of the chain are replaced with one or more double and/or triple bonds, $R_3$ being positioned on the ring para or meta to the bonding group X—Y, s and t, which may be identical or different, being 1 or 2, $R_4$ and $R_5$, which may be identical or different, represent a hydrogen atom, an acetyl radical, a benzoyl radical, a trimethylsilyl radical, a tert-butyldimethylsilyl radical or a tetrahydropyranyl radical, $R_6$ represents a hydrogen atom or a lower alkyl radical, W represents an oxygen or sulphur atom or an —NH— radical which can optionally be substituted with a lower alkyl radical, $R_7$ represents a hydrogen atom or a lower alkyl radical, $R_8$ represents a hydrogen atom, a lower alkyl radical or a halogen atom, and the optical and geometrical isomers of the said compounds of formula (I), and salts thereof.

2. A compound according to claim 1, in the form of a salt of an inorganic or organic acid.

3. A compound according to claim 1, wherein the lower alkyl radicals are selected from the group consisting of methyl, ethyl, isopropyl, tert-butyl and hexyl radicals.

4. A compound according to claim 1, wherein the cycloalkyl radical corresponds to a cyclopropyl, cyclopentyl or cyclohexyl radical.

5. A compound according to claim 1, wherein the halogen atom corresponds to a fluorine, chlorine or bromine atom.

6. A compound according to claim 1, selected from the group consisting of:

(E)-7-[5-(3,4-bis-hydroxymethyl-phenoxymethyl)-2-thienyl]-3-ethyloct-6-en-3-ol, (E)-7-[4-(3,4-bis-hydroxymethyl-phenoxymethyl)-2-thienyl]-3-ethyloct-6-en-3-ol, (E)-7-[2-(3,4-bis-hydroxymethyl-phenoxymethyl)-4-thienyl]-3-ethyloct-6-en-3-ol, (E)-7-[5-(3,4-bis-hydroxymethyl-phenoxymethyl)-3-pyridyl]-3-ethyloct-6-en-3-ol, (E)-7-[6-(3,4-bis-hydroxymethyl-phenoxymethyl)-2-pyridyl)-3-ethylnon-6-en-3-ol, (E)-7-[5-(3,4-bis-hydroxymethyl-phenoxymethyl)-2-thienyl]-3-ethylnon-6-en-3-ol, (4E,6E)-7-[5-(3,4-bis-hydroxymethyl-phenoxymethyl)-2-thienyl]-3-ethylnona-4,6-dien-3-ol, (3E,5E)-6-[5-(3,4-bis-hydroxymethyl-phenoxymethyl)-2-thienyl]-1,1,1-trifluoro-2-trifluoromethylocta-3,5-dien-2-ol, (4E,6E)-7-[5-(3,4-bis-hydroxymethyl-phenoxymethyl)-2-thienyl]-1,1,1,2,2-pentafluoro-3-pentafluoroethylnona-4,6-dien-3-ol, (E)-7-[5-(3,4-bis-hydroxymethyl-phenoxymethyl)-3-thienyl]-3-ethyl-4,4-dimethylnon-6-en-3-ol, (E)-7-{5-[2-(3,4-bis-hydroxymethyl-phenyl)ethyl]-2-thienyl}-3-ethylnon-6-en-3-ol, (4E,6E)-7-{5-[2-(3,4-bis-hydroxymethyl-phenyl)ethyl]-2-thienyl}-3-ethylnona-4,6-dien-3-ol, (3E,5E)-6-{5-[2-(3,4-bis-hydroxymethyl-phenyl)ethyl]-2-thienyl}-1,1,1-trifluoro-2-trifluoromethylocta-3,5-dien-2-ol, (4E,6E)-7-{5-[2-(3,4-bis-hydroxymethyl-phenyl)ethyl]-2-thienyl}-1,1,1,2,2-pentafluoro-3-pentafluoroethylnona-4,6-dien-3-ol, (4E,6E)-7-[5-(3,4-bis-hydroxymethyl-benzylamino)-2-thienyl]-3-ethylnona-4,6-dien-3-ol, (4E,6E)-7-{5-[(3,4-bis-hydroxymethyl-benzyl)methylamino]-2-thienyl}-3-ethylnona-4,6-dien-3-ol, (4E,6E)-7-{5-[(3,4-bis-hydroxymethyl-benzyl)propylamino]-2-thienyl}-3-ethylnona-4,6-dien-3-ol, (E)-7-[4-(3,4-bis-hydroxymethyl-phenoxymethyl)-2-thienyl]-3-ethylnon-6-en-3-ol, (4E,6E)-7-[4-(3,4-bis-hydroxymethyl-phenoxymethyl)-2-thienyl]-3-ethylnona-4,6-dien-3-ol, (3E,5E)-6-[4-(3,4-bis-hydroxymethyl-phenoxymethyl)-2-thienyl]-1,1,1-trifluoro-2-trifluoromethylocta-3,5-dien-2-ol, (E)-7-{4-[2-(3,4-bis-hydroxymethyl-phenyl)ethyl]-2-thienyl}-3-ethylnon-6-en-3-ol, (4E,6E)-7-{4-[2-(3,4-bis-hydroxymethyl-phenyl)ethyl]-2-thienyl}-3-ethylnona-4,6-dien-3-ol, (3E,5E)-6-{4-[2-(3,4-bis-hydroxymethyl-phenyl)ethyl]-2-thienyl}-1,1,1-trifluoro-2-trifluoromethylocta-3,5-dien-2-ol, (E)-7-[5-(3,4-bis-hydroxymethyl-phenoxymethyl)-3-thienyl]-3-ethylnon-6-en-3-ol, (4E,6E)-7-[5-(3,4-bis-hydroxymethyl-phenoxymethyl)-3-thienyl]-3-ethylnona-4,6-dien-3-ol, (3E,5E)-6-[5-(3,4-bis-hydroxymethyl-phenoxymethyl)-3-thienyl]-1,1,1-trifluoro-2-trifluoromethylocta-3,5-dien-2-ol, (E)-7-{5-[2-(3,4-bis-hydroxymethyl-phenyl)ethyl]-3-thienyl}-3-ethylnon-6-en-3-ol (4E,6E)-7-{5-[2-(3,4-bis-hydroxymethyl-phenyl)ethyl]-3-thienyl}-3-ethylnona-4,6-dien-3-ol, and (3E,5E)-6-{5-[2-(3,4-bis-hydroxymethyl-phenyl)ethyl]-3-thienyl}-1,1,1-trifluoro-2-trifluoromethylocta-3,5-dien-2-ol.

7. A compound according to claim 1, which has at least one of the following characteristics:

$R_1$ represents a —$CH_3$ or —$(CH_2)_s$OH radical, $R_2$ represents a radical —$(CH_2)_t$OH, X—Y represents a bonding group of formula (b), (c), (h) or (g), and $R_3$ is selected from the group consisting of
an alkyl or alkenyl chain of 4 to 8 carbon atoms substituted with at least one hydroxyl radical and at least one lower alkyl radical,
or an alkyl or alkenyl chain of 4 to 8 carbon atoms substituted with at least one hydroxyl radical, at least one lower alkyl radical and at least one $CF_3$ radical.

8. A method for the treatment:

of dermatological complaints associated with a keratinization disorder which has a bearing on differentiation and on proliferation, of other types of keratinization disorders, of other dermatological complaints with an inflammatory and/or immunoallergic component, with or without cell proliferation disorders, of dermal or epidermal proliferations, whether benign or malignant and whether they are of viral origin or otherwise, of other dermatological disorders comprising lupus erythematosus, immune bullosis and collagen diseases, of dermatological or general complaints with an immunological component, of disorders of sebaceous function, of skin disorders due to exposure to UV radiation, aging of the skin, whether it is light-induced or chronological aging, or pigmentations and actinic keratoses, or any pathologies associated with chronological or actinic aging, of cicatrization disorders or stretchmarks, of inflammatory complaints comprising arthritis, any complaint of viral origin on the skin or generally, of ophthalmological disorders, of cancerous or pre-cancerous states of cancers presenting or possibly being induced by vitamin D receptors, of alopecia of various origins, of immune system or autoimmune diseases, or of immune rejection, of endocrine complaints, of complaints associated with abnormal management of intracellular calcium, and of pathologies in which calcium metabolism is involved;

of vitamin D deficiencies and other mineral homeostasis complaints in plasma and bone, of complaints of the cardiovascular system, or of non-insulin-dependent diabetes, comprising administering an effective amount of at least one compound according to claim 1 to a patient in need of such treatment.

9. The method of claim 8, wherein said vitamin D deficiency or other mineral homeostasis complaint is rickets, osteomalacia, or osteoporosis.

10. A pharmaceutical composition comprising, in a pharmaceutically acceptable support, at least one of the compounds as defined in claim 1.

11. A pharmaceutical composition according to claim 10, wherein the concentration of compound(s) is between 0.0001% and 5% by weight relative to the total weight of the composition.

12. A cosmetic composition, comprising, in a cosmetically acceptable support, at least one of the compounds as defined in claim 1.

13. A cosmetic composition according to claim 12, wherein the concentration of compound(s) is between 0.001% and 3% by weight relative to the total weight of the composition.

14. A method for body or hair hygiene comprising administering an effective amount of at least one compound according to claim 1 to a patient in need thereof.

* * * * *